United States Patent [19]
Morris et al.

[11] Patent Number: 6,127,117
[45] Date of Patent: Oct. 3, 2000

[54] PRIMER SETS FOR ANALYZING CYTOCHROME P450 ISOENZYMES EXPRESSION

[75] Inventors: Dale Lynn Morris, Ballwin, Mo.; Julio Cesar Davila, Gurnee, Ill.

[73] Assignee: G. D. Searle & Co., Chicago, Ill.

[21] Appl. No.: 08/855,583

[22] Filed: May 13, 1997

Related U.S. Application Data

[63] Continuation-in-part of application No. 08/645,067, May 13, 1996, abandoned.

[51] Int. Cl.[7] .............................. C12Q 1/68; C12P 19/34; C07H 21/04
[52] U.S. Cl. ....................... 435/6; 435/91.2; 435/91.51; 536/22.1; 536/24.33
[58] Field of Search ............................... 536/22.1, 24.33; 435/91.2, 91.51, 6

[56] References Cited

U.S. PATENT DOCUMENTS 4,683,202  7/1987  Mullis et al. .............................. 435/91

FOREIGN PATENT DOCUMENTS

WO30766  11/1995  WIPO .............................. C12Q 1/00

OTHER PUBLICATIONS

Yabusaki et al. Nucleotide sequence of a full-length cDNA coding for 3-methylcholanthrene-induced rat liver cytochrome P-450MC, Nucleic acid research vol. 12(6). pp. 2929–2938, 1984.

Kawajiri et al. Coding nucleotide sequence of 3-methylcholanthrene-inducible cytochrome P-450d cDNA from rat liver, Proc. Natl. Acad. Sci. USA vol. 81, pp. 1649–1653, 1984.

Mizukami et al. Gene structure of a phenobarbital-inducible cytochrome P-450 in rat liver, Proc. Natl. Acad. Sci. USA, vol. 80, pp. 3958–3962, 1983.

Yoshioka et al. Structural analysis and specific expression of microsomal cytochrome P-450(M-1) Mrna in male rat livers, J. Biol. Chem. vol. 262(4), pp. 1706–1711, 1987.

Song et al. Complementary DNA and protein sequences of ethanol-inducible rat and human cytochrome P-450s, J. Biol. Chem. vol. 261(35), pp. 16689–16697, 1966.

Miyata et al. Structure of a gene and cDNA of a major constitutive form of testosterone 6B-hydroxylase (P450/6BA) encoding CYP3A2: comparison of the cDNA with P450PCN2, Arch. Biochem. Biophys. vol. 314(2), pp. 351–359, 1994.

Hardwick et al. Isolation, complementary DNA sequence, and regulation of rat hepatic lauric acid w-hydroxylase (cytochrome P450), J. Biol. Chem. vol. 262(2), pp. 801–810, 1987.

Fufii–Kuriyama et al. Primary structure of a cytochrome P-450:coding nucleotide sequence of phenobarbital-inducible cytochrome p-450 cDNA from rat liver, Proc. Natl. Acad. Sci. vol. 79, pp. 2793–2797, 1982.

Hellmod et al. Development and endocrine regulation of P450 isoforms in rat breast, Molecular Pharmacology vol. 48, pp. 630–638, 1995.

Hakkola et al. Expression of xenobiotic-metabolizing cytochrome p450 forms in human adult and fetal liver, Biochemical Pharmacology, vol. 48(1), pp. 59–64, 1994.

Molecular Pharmacology, vol. 46, No. 5 (Nov. 1994) 922–928.

Archives of Biochem. and Biophys., vol. 237 (Feb. 1985) 465–476.

J. Biochem., vol. 271, No. 1 (Oct. 1990) 113–119.

Biochemical Pharmacology, vol;. 52 (1996) 781–792.

Cavicchioli L. et al., "Choline acetyltransferase messenger RNA expression in developing and adult rat brain: regulation by nerve growth factor" Mol. Brain Research, vol. 9, Mar. 1991 pp. 319–325.

Waxmann et al., "Gene-specific oligonucleotide probes for a, u, t and microsomal rat glutathione S-transferases: analysis of liver transferase expression and its modulation by hepatic enzyme inducers and platinum anticancer drugs" Cancer Research, vol. 52,—Oct. 15, 1992, pp. 5797–5802.

Nuwaysir E.F. et al., "Phase II enzyme expression in rat liver in response to the antiestrogen tamoxifen", Cancer Research, vol. 56,—Aug. 10, 1996, pp. 3704–3710.

*Primary Examiner*—W. Gary Jones
*Assistant Examiner*—Joyce Tung
*Attorney, Agent, or Firm*—Fitzpatrick, Cella, Harper & Scinto

[57] ABSTRACT

Hepatocyte culturing system, primer sets and an analytical method for selectively detecting and quantitatively assessing the levels of mRNA expression of the major isoenzymes of cytochrome P450 (CYP450 1A1, 1A2, 2B1/2, 2C11, 2E1, 3A1, 3A2 and 4A1), fatty acyl-CoA oxidase (FACO) and select Phase II conjugating enzymes (UDPGT, GST and ST) in the rat using specific 5' and 3' oligonucleotide primers and reverse transcriptase-polymerase chain reaction. The method closely reproduces the expression obtained from rat liver tissue following treatment with the same enzyme inducers. Constitutive and inducible expression was maintained by resuspending, culturing and then overlaying adult rat hepatocytes with an extracellular matrix such as Matrigel®.

11 Claims, 27 Drawing Sheets

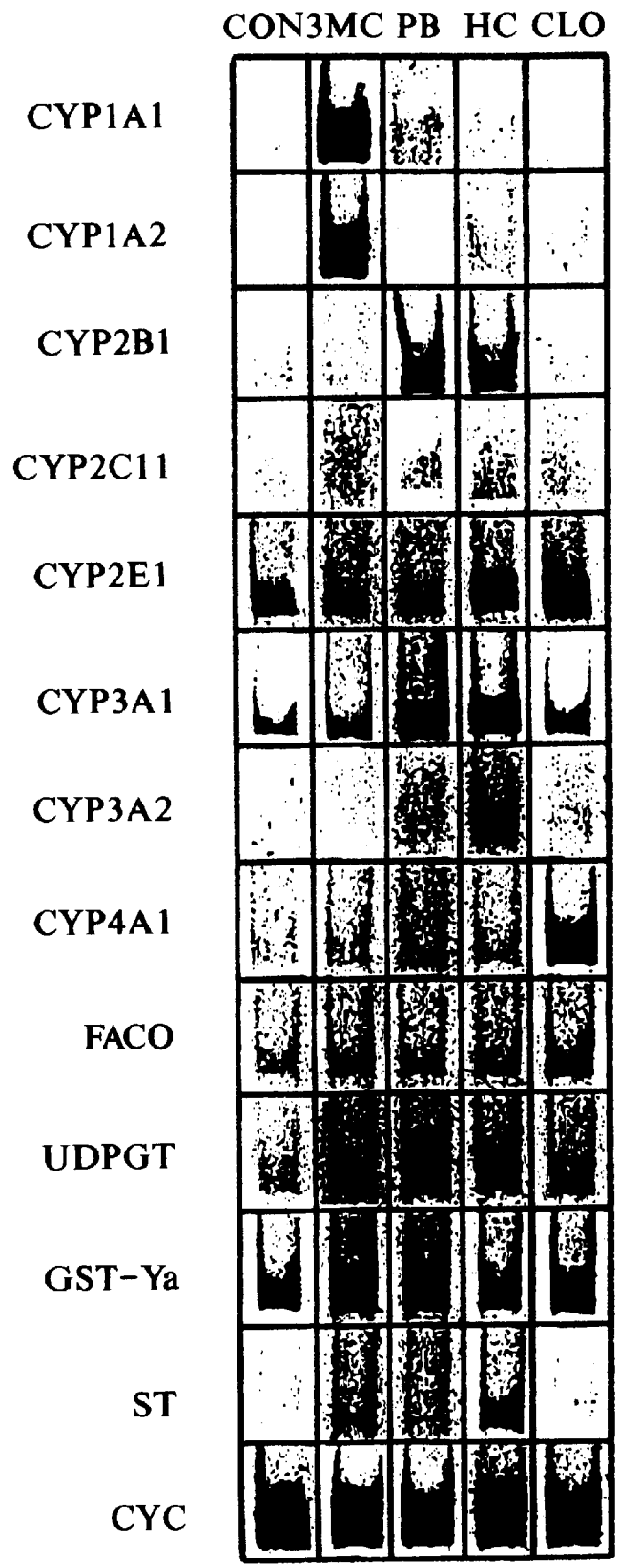
FIG. IB

PRIMER SETS FOR ANALYZING CYTOCHROME P450 ISOENZYMES EXPRESSION

This application is a continuation in part of Ser. No. 08/645,067, now abandoned, filed May 13, 1996.

BACKGROUND OF THE INVENTION

1. Field of the Invention

This invention relates to a method of detecting expression of isoenzymes of cytochrome P450 (CYP450) and Phase II conjugating enzymes in the rat. More specifically, this invention relates to specific 5' and 3' specific oligonucleotide primers, as well as a method of using the same with reverse transcriptase-polymerase chain reaction (RT-PCR) to detect mRNA expression of the major isoenzymes of CYP450 and fatty acyl-CoA oxidase in the rat. This invention includes the development of an in vitro culture system using rat hepatocytes which has been optimized for expression of both cytochrome P450 and Phase II conjugating enzymes.

2. Description of the Prior Art

The cytochrome P450 mixed function oxidases (MFO) are a group of enzymes which are predominantly expressed within the liver, kidney, lung and intestine of mammalian species where they play an important role in the oxidative metabolism of both endogenous and exogenous (xenobiotic) compounds. The role of the various members of this enzyme superfamily in the metabolism of drugs and chemicals, as well as their potential role in the generation of toxic metabolites and chemical-induced carcinogenesis, is well established.

In particular, induction of specific CYP450 isoforms has been associated with drug-drug interactions in humans and increases in liver weight, proliferation of the endoplasmic reticulum and non-genotoxic liver carcinogenicity and tumorigenicity in rodents. Guengerich, *Cancer Res* 48:2946–2954, 1988; Lake, *Ann Rev Phaacol Toxical* 35: 483–507, 1995; Hankinson, *Ann Rev Pharmacol Toxicol* 35:307–340, 1995; Parkinson, *Toxicol Pathol* 24:45–57, 1996; and Kirby et al., *Toxicol Pathol* 24:458–467, 1996; and Burchell et al., *Pharmacol Ther* 43:261–289, 1989.

In addition to CYP450 enzymes, Phase II enzymes, which are involved in the conjugation of xenobiotics and their metabolites for excretion, have also been associated with the bioactivation of xenobiotics to toxic and tumorigenic metabolites. Parkinson, *Casarett & Doull's Toxicology, The Basic Science of Poisons* (Ed., Klaasen CD), 5th Edn, pp 113–186, McGraw-Hill, Inc., New York, 1996; Boberg, *Cancer Res.* 43:5163–5173, 1983; Curran et al., *Endocrine Rev* 12:135–150, 1991; Bock, *Pharmacogenetics* 4:209–218, 1994; and Monks, et al., *Toxicol Appl Pharmacol* 106:1–19, 1990.

Examples of these Phase II enzymes include uridine diphosphate-glucuronosyltransferases (UDPGT), glutathione-S-transferases (GST), and sulfotransferases (ST). Historically, in vivo models are commonly used for the study of chemical-induced enzyme expression and hepatotoxicity. However, this approach is costly, time consuming and requires large quantities of test material.

Several approaches have been used to monitor the regulation of cytochrome P450 (CYP450) enzymes following exposure to xenobiotics. The approach most often employed is to measure the enzymatic profiles of microsomal protein fractions using enzyme selective substrates. Although this technique is useful for the study of substrate specificities, enzyme kinetics, and metabolism of chemicals there are several disadvantages which can limit the application of this technique in assessing the biochemical regulation of these enzymes. Two important disadvantages are that CYP450 enzyme activity requires additional cofactors (e.g., requirement for the presence of heme) and can show non-selectivity for, or be inhibited by certain chemical substrates (e.g., ketoconazole and metyrapone), resulting in potentially misleading or inaccurate assessments of enzyme activity.

Today, the chemical industry (Pharmaceutical and Chemical manufacturers) recognize the value in developing in vitro techniques to assess the safety and efficacy of drugs and chemicals at an early stage of development. In vitro techniques most commonly used to study the expression of hepatic metabolizing enzymes and cytotoxicity include precision-cut liver slices (Brendel et al., *Methods in Toxicology* (Ed. Tyson and Frazier), Vol 1 A. pp 222–243, Academic Press Inc. NY., 1993; and Gandolfi et al., *Toxicol. Pathol.* 24:58–61, 1996), primary cultures of hepatocytes and immortalized cell lines. Donato et al., *In Vitro Cell Develop Biol* 30A:574–580, 1994; and MacDonald et al., *Human and Exp Toxicol* 13:439–444, 1994.

However, without exception, these in vitro systems have limitations in their applications. For example, continuously dividing cell lines fail to preserve their ability to express or induce specific Phase I and II metabolizing enzymes, resulting in enzymatic activities which are either absent or too low to be measured. In addition, a loss of more than 50% of the total metabolizing enzyme levels have been reported within 24 hr of culture using non-dividing whole cell systems (e.g., precision-cut tissue slices and primary cell culture systems). Guzelian et al., *Drug Metabol Rev* 10:793–809, 1989; Waxman et al., *Biochem J.* 271:113–119, 1990; Paine, *Chem Biol Interac* 747:1–31, 1990; and Dunn et al., *Biotechnol Prog* 7:237–245, 1991.

A number of reports have demonstrated that primary hepatocytes cultured under conditions which restore normal cell's morphology and liver specific gene expression, can respond to xenobiotics with induction of specifically inducible CYP450 enzymes to levels comparable with those achieved in vivo. Bissel et al., *Ann NY Acad Sci* 349:85–98, 1980; Isom et al., *J Cell Biol* 105:2877–2885, 1987; Ben-Ze'ev et al., *Proc Natl Acad Sci* 85:2161–2165, 1988; Schuetz et al., *J Cell Physiol* 134:309–323, 1988; Musat et al., *Hepatology* 18:198–205, 1993; Arterburn et al., *Hepatology* 21:175–187, 1995; Kocarek et al., *Mol Pharmacol* 43:328–334, 1992; Sidhu et al., *In Vitro Toxicol* 7:225–242, 1994; and Zurlo et al., *In Vitro Cell Develop Biol* 32:211–220, 1996.

Examples of these cell culture conditions include the use of an extracellular matrix (ECM), Schuetz et al., *J Cell Physiol* 134:309–323, 1988, chemically defined culture media conditions and hepatocytes co-cultured with non-parenchymal cells. Begue et al., *Hepatol* 4:839–842, 1984; Rogiers et al., *Biochem Pharmacol* 40:1701–1706, 1990; Donato et al., *In vitro Cell Develop Biol* 30A:825–832, 1994; Guzelian et al., *Proc Natl Acad Sci* 85:9783–9787, 1988; Kocarek et al., Mol Pharmacol 38:440–444, 1990; Kocarek, *In Vitro Cell Develop Biol* 29A:62–66, 1992; and Kocarek et al., *Biochem Pharmacol* 48:1815–1822, 1994.

More recently, polyclonal and monoclonal antibodies have been generated against various isoenzymes of CYP450 found in rat, thereby allowing for a more selective and defined analysis of CYP450 expression, Parkinson et al., *Meth. Enzymol.* 206: 233–245, 1991. This approach to monitoring changes in CYP450 isoenzymes has many advantages over those which monitor enzyme activity, particularly with regard to enzymes which are regulated post-translationally (e.g., CYP2E1). However, the success of this approach is dependent on the quality and availability of reagents (e.g., polyclonal versus monoclonal antibodies) and may lack the specificity for determining enzyme subtype expression (e.g., CYP3A1 and CYP3A2). Moreover, the generation of antibodies and the measurement of proteins using Western immunoblot analysis are both labor intensive and time consuming and cannot be readily implemented when new enzymes are identified.

A number of reports have described use of ECM systems in studying the expression of liver-specific gene regulation in primary rat hepatocytes, Kocarek et al., *Drug Metabol Dispos* 23:415–421, 1995, Waxman et al., *Biochem J* 271:113–119, 1990, Sidhu et al., *In Vitro Toxicol* 7:225–242, 1994, and Zurlo et al., *In Vitro Cell Develop Biol* 32:211–220, 1996.

These reports indicate that 1) hepatocyte genes expression decreases markedly after cell isolation, 2) hepatocyte isolation procedures result in altered expression of CYP450 mRNAs, 3) hepatocyte gene expression is restored after several days in culture, 4) the maintenance and/or inducibility of one or more P450 isoenzymes are lost during the first 48 hr in culture, and 5) hepatocytes cultured on extracellular matrix-coated plates, and under specific culture conditions (e.g., modified Chee's medium) maintain a wide range of CYP450 isoenzyme expression and the activities of certain CYP450 enzymes are enhanced following exposure to CYP450 inducing agents.

Accordingly, the present inventors sought to develop a feasible, reproducible and simple in vitro system for evaluating xenobiotics as CYP450 enzyme inducers, which could be used for routine toxicology applications. The inventors have optimized the ECM system to study and monitor a broad range of liver biotransformation enzymes at the mRNA and protein levels. In contrast with the classical methods in which hepatocytes are seeded on ECM-coated dishes (e.g., collagen or Matrigel®), and then maintained on Matrigel® (sandwich or overlay), the present invention optimizes rat hepatocyte culture conditions for enzyme expression by suspending the hepatocytes in Matrigel® before seeding them in culture. Rat hepatocytes cultured under these culture conditions show an enhanced level of expression of a variety of liver metabolizing enzymes within 24 hr after initial plating in response to chemical inducers. This permits induction and maintenance in culture of liver-specific biotransformation enzyme genes for greater than seven days at both the mRNA and protein levels. More importantly, rat hepatocytes responded very similar to adult rat liver when exposed repeatedly to the same or similar types of inducing agents.

The inventors have demonstrated this improved rat hepatocyte culture system by utilizing prototypical CYP450 enzyme inducers, including PB as an inducer of the CYP2B subfamily, HC as an inducer of the CYP3A subfamily, 3MC as an inducer of the CYPLA subfamily and CLO as an inducer of the CYP4A subfamily (and FACO). In all of the in vitro experiments conducted, substantially complete agreement in the detection of CYP450 gene expression was found between the RT-PCR and western immunoblotting techniques.

These results show that CYP450 enzyme expression is regulated primarily at the mRNA level. Nebert, *Biochem Pharmacol* 47:25–37, 1994, Gonzalez et al., *Pharmacogenetics* 3:51–57, 1993 and Gonzalez et al., *FASEB J* 10:1112–1117, 1996. This is particularly true of the inducible forms the CYP450 enzymes, including CYP1A1/2, CYP2B1, CYP3A1/2 and CYP4A1. These enzymes are shown to be constitutively expressed at low or undetectable levels in this in vitro culture system but are markedly increased upon exposure to CYP450 inducing agents at both the mRNA and protein levels. The induction of these CYP450 enzymes involves transcriptional activation of the CYP450 genes, which may also involve message stabilization, resulting in an increase in the levels of mRNA and newly synthesized protein.

The expression of CYP2E1 mRNA, which is constitutively expressed in vitro at both the mRNA and protein levels, is known to be increased generally by protein stabilization, although mRNA stabilization and/or increased efficiency of mRNA translation may also be involved. Hunt et al., *Xenobiotica* 21:1621–1631, 1991 and Raucy et al., *Critical Rev Toxicol* 23:1–20, 1993.

CYP2C11, an adult male rat-specific CYP450 isoform, has been shown to be constitutively expressed and noninducible in male rat liver. Waxman et al., *Biochem* 88:6868–6871, 1991, Morohashi et al., *FASEB J* 10:1569–1577, 1996 and Prough et al., *FASEB J* 10:1369–1377, 1996. This enzyme has been shown to be partially regulated by androgenic hormones in vivo and the disruption of circulating levels of growth hormone patterns by xenobiotics can decrease expression of this enzyme.

As expected, CYP2C11 was found to be constitutively expressed at low levels and noninducible by the CYP450 inducing agents in male rat hepatocytes cultured under the present conditions.

In agreement with other investigators, we have observed that maintenance of 3MC-mediated induction of the CYP1A1 and CYP1A2 enzymes, PB-mediated induction of the CYP2B11 and CYP3A1 enzymes, HC-mediated induction of CYP3A1, CYP3A2, and CYP2B enzymes, and CLO-mediated induction of the CYP4A1 and FACO enzymes in rat hepatocytes, is critically dependent on the presence of an ECM (e.g., Matrigel®). Waxman et al., *Biochem J* 271:113–119, 1990, Jauregui et al., *Xenobiotica* 21:1091–1106, 1991, and Kocarek et al., *Mol Pharmacal* 43:328–334, 1992.

We have also observed that CYP3A1 and CYP3A2 are induced by both steroid and PB-type inducers and the induction is dependent on the concentration of the inducer in the medium. For example, treatment of hepatocyte cultures with hydrocortisone, at concentrations as low as 10 $\mu$M, results in the induction of the CYP3A1 and CYP3A2 and CYP2B1 enzymes at mRNA level, whereas lower doses (e.g, 0.1 $\mu$M) did not affect enzyme expression. Like CYP3A1, CYP2B1 mRNA levels increased in a dose-related manner in the presence of HC.

Another significant finding was the effect of CLO on hepatocytes cultured on Matrigel®. We have found, in agreement with in vivo studies, that CLO increased the expression of the CYP4A1, CYP2E1 and FACO enzymes at the mRNA level. Tugwood et al., *EMBO J* 11:433–439, 1992, Gulick et al., *Proc Natl Acad Sci* 91:11012–11016, 1994 and Johnson et al., *FASEB J* 10:1241–1248, 1996.

This finding suggests that activation of peroxisomal enzymes can occur in this system, that CLO causes an increase in the expression of multiple CYP450 enzymes and that CLO can up-regulate the expression of the CYP2E1 enzyme at the mRNA level. The effect of CLO on CYP2E1 expression has been observed following in vivo exposures.

Phase II enzymes are of considerable importance in toxicology. The pharmacological and toxicological effect of many reactive endogenous and exogenous compounds depends on their rate of formation and elimination, which involves Phase II conjugating enzymes such as UDPGT, GST and ST. The absence or presence of these enzymes has been associate with carcinogenicity and adverse reactions of certain drugs and chemicals.

To further characterize our in vitro system, we have studied the effects of liver enzyme inducers on the expression of UDPGT, GST-Ya and ST at the mRNA level. We have found that these enzymes are constitutively expressed and induced by prototypical CYP450 inducers, similar to the inducible CYP450 isoforms.

In contrast with CYP450 enzymes, Phase II enzyme expression has been scarcely studied in cell culture. However, several reports have shown that Phase II conjugating enzymes can be maintained in culture using modified culture conditions (Grant et al., *Biochem Pharmacol* 35:2979–2982, 1986, Vandenberghe et al., *In vitro Cell Develop Biol* 24:281–288, 1988 and Vandenberghe et al., *Biochem Pharmacol* 37:2481–2485, 1988), ECM (Kane et al., *In vitro Cell Develop Biol* 27A:953–960, 1996, Judah et al., *Toxic Appl Pharmacol* 125:27–33, 1994) or co-culture systems. Rogiers et al., *Biochem Pharmacol* 40:1701–1706, 1990.

We have found that these enzymes can be maintained and induced in hepatocytes cultured with Matrigel®. We have found that phenobarbital, as well as hydrocortisone, markedly enhance the expression of these enzymes. The regulation of these Phase II conjugating enzymes by glucocorticoids has been previously demonstrated in cultured rat hepatocytes. The data presented here support the potential utility of this culture system for assessing the induction of Phase II conjugating enzymes in the rat by new chemical entities (NCE).

SUMMARY OF THE INVENTION

An object of the present invention is to selectively assay CYP450 expression in both in vivo (whole animal) and in vitro (hepatocyte or other expression system) systems.

Another object of the present invention is to assay CYP450 expression without regard to enzyme subtype.

A still other object of the present invention is to provide an in vitro rat hepatocyte culturing system (and analytical method) for determining the effects of xenobiotics on the expression of adult rat liver CYP450 and Phase II conjugating enzymes.

These objects and others are provided by the present invention, which is a method of using reverse transcriptase-polymerase chain reaction (RT-PCR) with particular PCR primers to detect and quantitate the levels of mRNA expression of the major isoenzymes of CYP450, fatty acyl-CoA oxidase (FACO) and select Phase II conjugating enzymes in both in vivo and in vitro systems. This invention also relates to the specific oligonucleotide 5' and 3' PCR primers which can be used to amplify DNA encoding selected CYP450 isoenzymes, FACO and select Phase II conjugating enzymes, as well as kits containing sets of the primer. This invention also includes the development of an in vitro rat hepatocyte culturing system which has been optimized for use in determining chemical-mediated induction of CYP450 and Phase II conjugating enzymes.

As a result of the present invention, expression of CYP450 enzymes can be efficiently and selectively measured at the mRNA level in any tissue, especially following exposure to drugs and chemicals. This technique is extremely sensitive, quantitative and can be automated for diagnostic applications. This cell culture system and analytical methodology is also applicable to routine toxicology screening for the assessment of chemically-induced changes in liver CYP450 enzyme expression.

DETAILED DESCRIPTION OF THE INVENTION

Figure 1A:
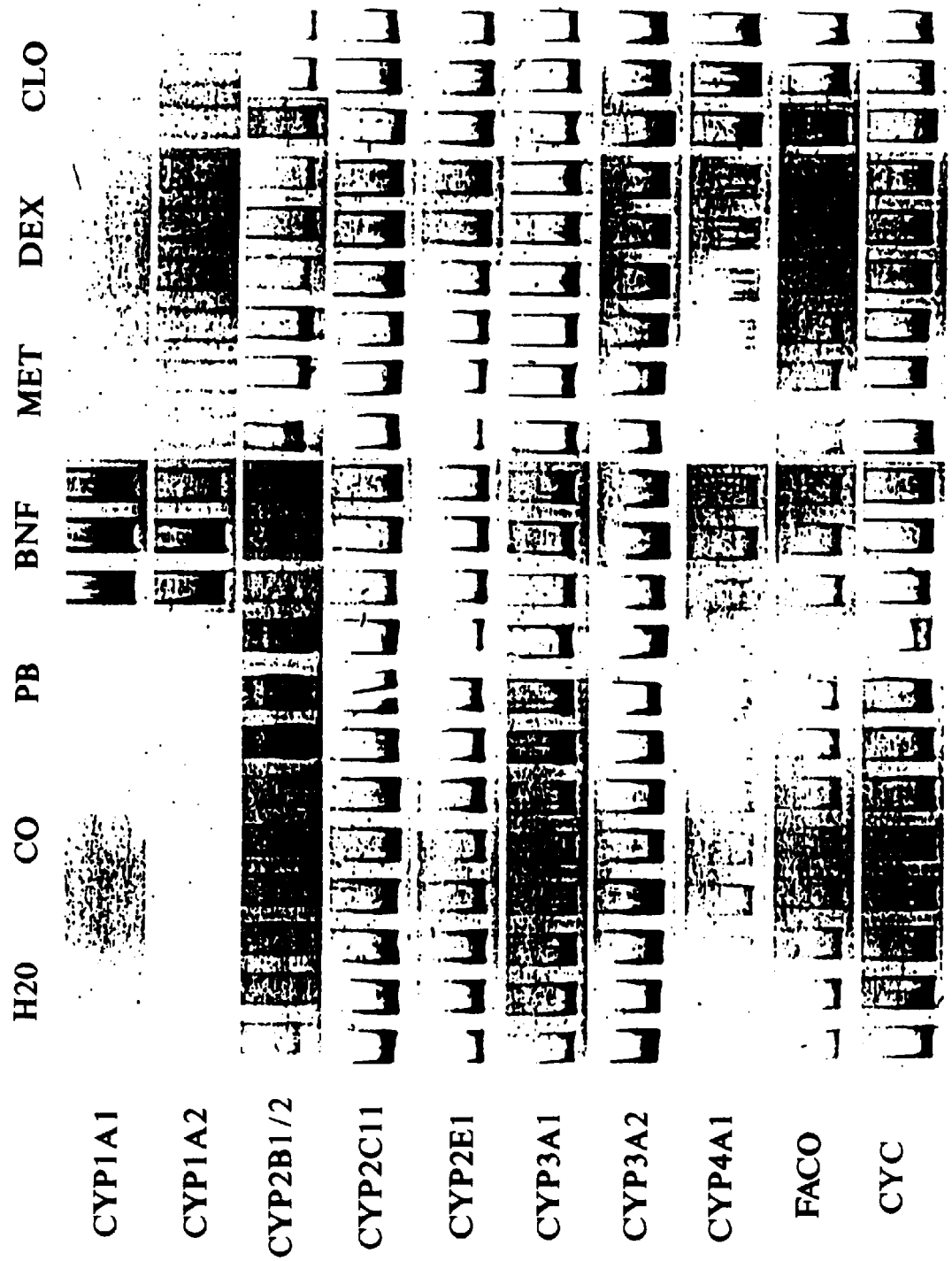
FIGS. 1a and 1b illustrate the results obtained using RT-PCR to assess the levels of CYP450 FACO and Phase II mRNA expression in the livers of male rats exposed to various chemical inducers of CYP450 in in vivo and in vitro, respectively.
Figure 2A:
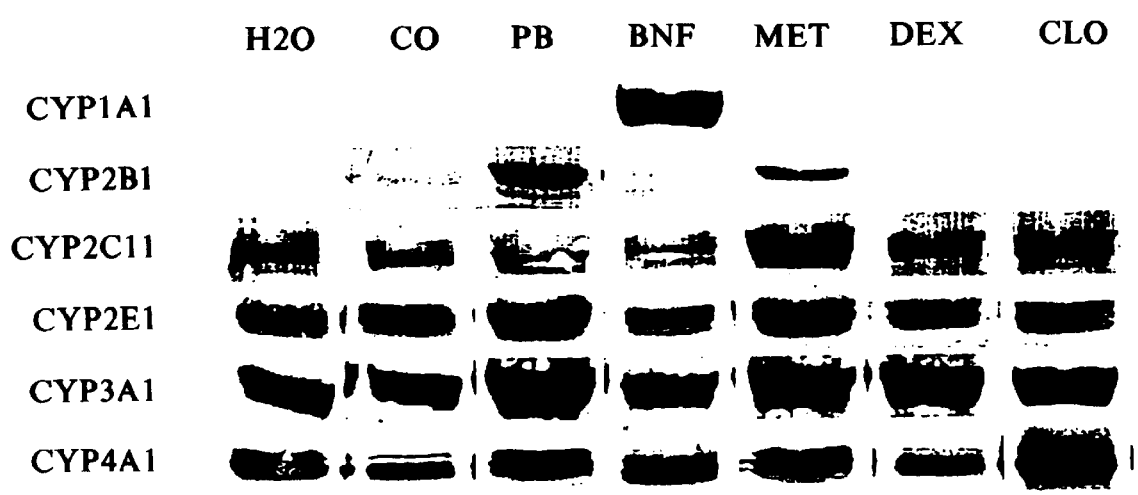
FIGS. 2a and 2b illustrate the results obtained using Western immunoblotting to assess the levels of CYP450 apoprotein in the livers of male rats exposed to various chemical inducers of CYP450 in in vivo and in vitro, respectively.
Figure 2B:
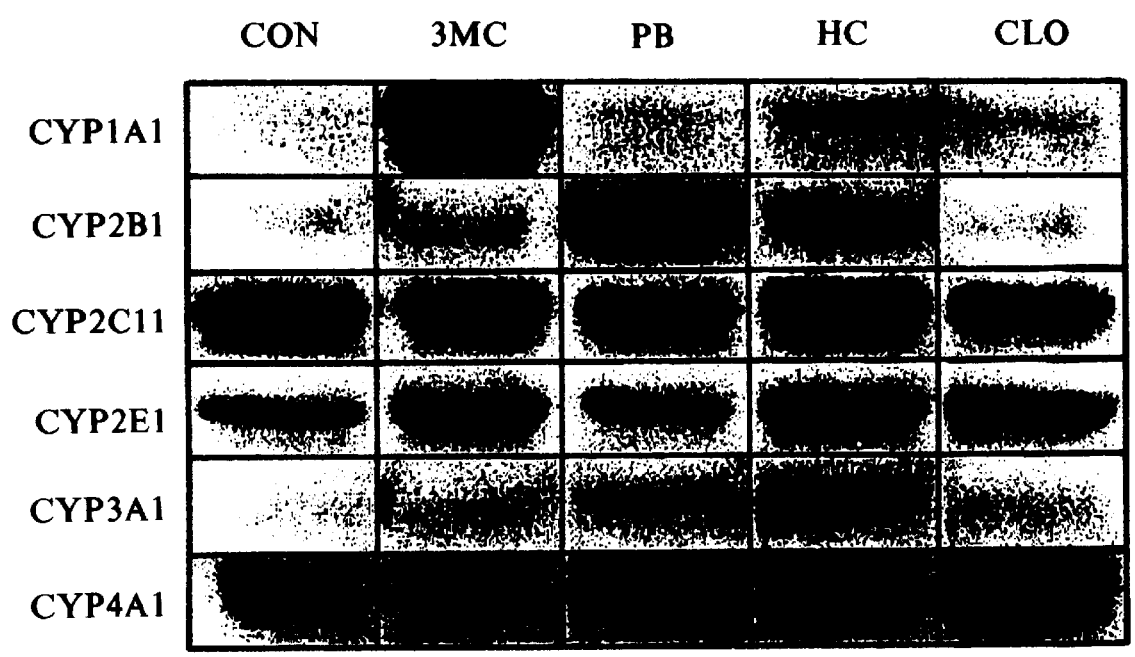

This invention is a method of detecting levels of mRNA expression of isoenzymes of cytochrome P450 mixed function oxidases (CYP450 MFOs) using reverse transcriptase-polymerase chain reaction and specific oligonucleotide PCR primers. The CYP450 MFOs present one of the body's most important mechanisms of defense against chemical-induced toxicity. This superfamily of catabolic enzymes oxidize both endogenous and exogenous (xenobiotic) compounds, converting them to hydrophilic metabolites which can be readily removed from the body.

In some instances however, metabolism of chemicals by the CYP450 enzymes may be undesirable or detrimental to the body. For instance, metabolism of certain compounds (e.g., acetaminophen) can lead to toxic or reactive intermediates, resulting in target organ toxicity and/or carcinogenic insult.

Furthermore, with chemical-based therapeutics, induction of CYP450 isoenzymes can lead to metabolism of and/or accelerated removal of drugs, which may limit their desired pharmacological actions. This phenomena, known as "autoinduction", can be problematic in drug discovery and an obstacle to the development of adequate therapeutics. Finally, species differences in metabolic capabilities of therapeutic candidates may suggest that responses in certain animal models are not relevant for man. Therefore, it is extremely important to monitor the expression of CYP450 isoenzymes in the early stages of drug discovery, to assist in the development of safe and effective therapeutics.

The level of expression of CYP450 isoenzyme and fatty acyl CoA oxidase is determined by quantitating amplified cDNA (mRNA) obtained through the use of oligonucleotide primer sets that specifically amplify for the individual isoenzyme or oxidase.

The primer set used for the amplification and detection of rat cytochrome P450 isoenzyme 1A1 contains oligonucleotides with the sequences (5') CTGGTTCTGGATACCCAGCTG (3')    (SEQ ID NO:1)

(5') CCTAGGGTTGGTTACCAGG (3')    (SEQ ID NO:2).

The primer set used for the amplification and detection of rat cytochrome P450 isoenzyme 1A2 contains oligonucleotides with the sequences (5') GTCACCTCAGGGAATGCTGTG (3')  (SEQ ID NO:3)

(5') GTTGACAATCTTCTCCTGAGG (3')  (SEQ ID NO:4).

The primer set used for the amplification and detection of rat cytochrome P450 isoenzyme 2B1/2 contains oligonucleotides with the sequences (5') GAGTTCTTCTCTGGGTTCCTG (3')  (SEQ ID NO:5)

(5') ACTGTGGGTCATGGAGAGCTG (3')  (SEQ ID NO:6).

The primer set used for the amplification and detection of rat cytochrome P450 isoenzyme 2C11 contains oligonucleotides with the sequences (5') CTGCTGCTGCTGAAACACGTG (3')  (SEQ ID NO:7)

(5') GGATGACAGCGATACTATCAC (3')  (SEQ ID NO:8)

The primer set used for the amplification and detection of rat cytochrome P450 isoenzyme 2E1 contains oligonucleotides with the sequences (5') CTCCTCGTCATATCCATCTG (3')  (SEQ ID NO:9)

(5') GCAGCCAATCAGAAATGTGG (3')  (SEQ ID NO:10).

The primer set used for the amplification and detection of rat cytochrome P450 isoenzyme 3A1 contains oligonucleotides with the sequences (5') ATCCGATATGGAGATCAC (3')  (SEQ ID NO:11)

(5') GAAGAAGTCCTTGTCTGC (3')  (SEQ ID NO:12).

The primer set used for the amplification and detection of rat cytochrome P450 isoenzyme 3A2 contains oligonucleotides with the sequences (5') CGACTTGGAACCCATAGAC (3')  (SEQ ID NO:13)

(5') GGCTTAGGGAGATTTGACATG (3')  (SEQ ID NO:14).

The primer set used for the amplification and detection of rat cytochrome P450 isoenzyme 4A1 contains oligonucleotides with the sequences (5') GGTGACAAAGAACTACAGC (3')  (SEQ ID NO:15)

(5') AGAGGAGTCTTGACCTGCCAG (3')  (SEQ ID NO:16).

The primer set used for the amplification and detection of rat fatty acyl-CoA oxidase contains oligonucleotides with the sequences (5') CTGTTATGATGCTGCAGACAGC (3')  (SEQ ID NO:17)

(5') ACACAGGTTCCTCAGCACAG (3')  (SEQ ID NO:18).

A primer set used for the amplification and detection of rat cyclophilin contains oligonucleotides with the sequences (5') CTTCGACATCACGGCTGATGG (3')  (SEQ ID NO:19)

(5') CAGGACCTGTATGCTTCAGG (3')  (SEQ ID NO:20).

Another primer set used for the amplification and detection of rat cyclophilin contains oligonucleotides with the sequences (5') CTTGTCCATGGCAAATGCTG (3')  (SEQ ID NO:21)

(5') GTGATCTTCTTGCTGGTCTTGC (3')  (SEQ ID NO:22).

The primer set used for the amplification and detection of rat CYP2B1 contains oligonucleotides with the sequences (5') CAACCCTTGATGACCGCAGT (3')  (SEQ ID NO:23)

(5') GGAAGTGTTCAGGATTGAAGC (3')  (SEQ ID NO:24).

The primer set used for the amplification and detection of rat UDP-Glucuronosyl-transferase contains oligonucleotides with the sequences (5') GCCTTCTCACTGCCTTGAAG (3')  (SEQ ID NO:25)

(5') GTCTTACGGCAACAAAAGAGGCAG (3')  (SEQ ID NO:26).

The primer set used for the amplification and detection of rat Glutathione-S-transferase contains oligonucleotides with the sequences (5') CTTGGCAAAAGACAGGACC (3')  (SEQ ID NO:27)

(5') GTTTTGCATCCATGGGAAGC (3')  (SEQ ID NO:28).

The primer set used for the amplification and detection of rat Sulfotransferase contains oligonucleotides with the sequences (5') CTTCAGTTCCAAGGCCAAGG (3')  (SEQ ID NO:29)

(5') GTGAAGTGATTCTTCCAGTC (3')  (SEQ ID NO:30).

Whereas most of the CYP450 enzymes have been shown to be constitutively expressed in rat liver, many are markedly increased in expression upon exposure to various chemicals. For example, in adults male rats, expression of CYP2C11 is constitutively expressed and noninducible in the liver whereas the expression of CYP450 1A1, 2B1, 2E1 and 4A1 are all selectively induced following exposure to various chemicals. This increase in CYP450 enzyme expression can occur via a number of mechanisms, including increased transcription, stabilization of mRNA and increased protein synthesis.

The present invention provides a rapid, high throughput, screening assay for the assessment of CYP450, especially in rat, which can be automated for routine toxicology applications. It is anticipated that the oligonucleotide primer sets can be present in a kit, alone or in combination with other elements, to screen any number of samples for the presence of one of, or a series of, CYP450 isoenzymes. A primer set kit may contain any one or more of the primer sets, in any combination, as needed for toxicology applications.

Using the technique known as RT-PCR, changes in CYP450 mRNA expression were measured as a surrogate to changes in apoprotein expression and substrate-specific enzymatic activity in the liver of chemically exposed rats. To illustrate the validity of this approach, several prototypical inducers of liver CYP450 enzymes were selected to determine the correlation between changes in mRNA, protein and enzymatic activity. The inducers included β-naphthoflavone (BNF) as an inducer of the CYP1A subfamily, phenobarbital (PB) as an inducer of the CYP2B subfamily, dexamethasone (DEX) as an inducer of the CYP3A subfamily and clofibrate (CLO) as an inducer of the CYP4A subfamily and fatty acyl-CoA oxidase. In addition, metyrapone (MET) was utilized to show the effects of an enzyme activity inhibitor on the expression of CYP450 isoenzymes.

Figures 1, 3A:
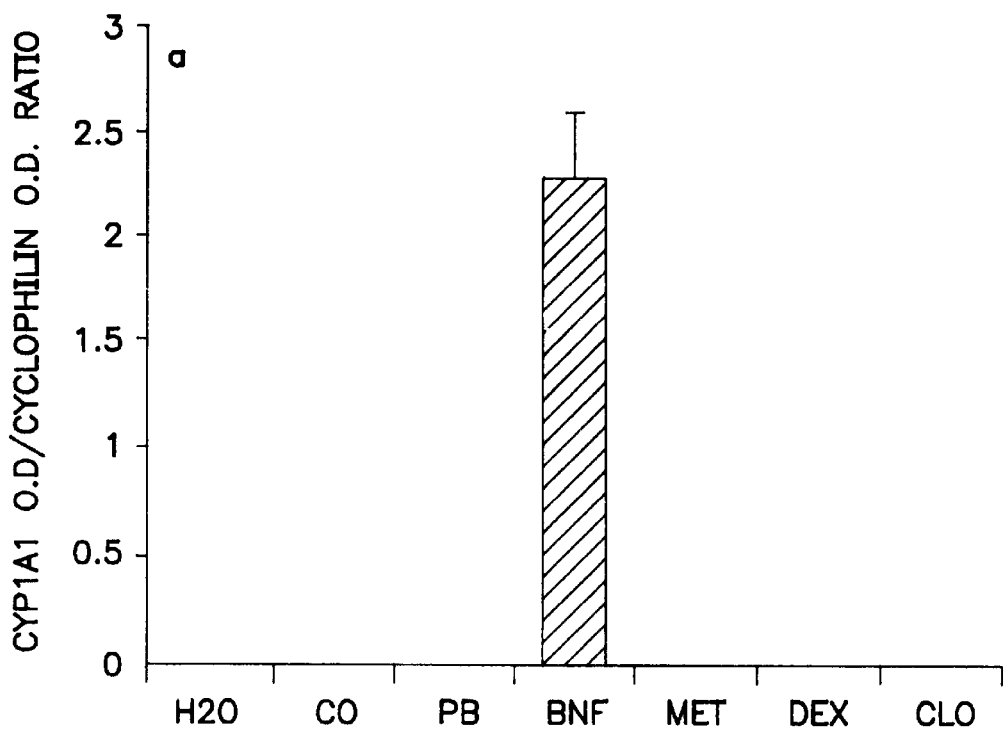
FIGS. 3a–3z illustrate the results obtained using RT-PCR, western Immunoblotting and substrate-specific enzyme activities to assess the levels of CYP450, FACO and Phase II enzyme expression in the livers of male rats exposed to various chemical inducers.
Figures 2, 3A:
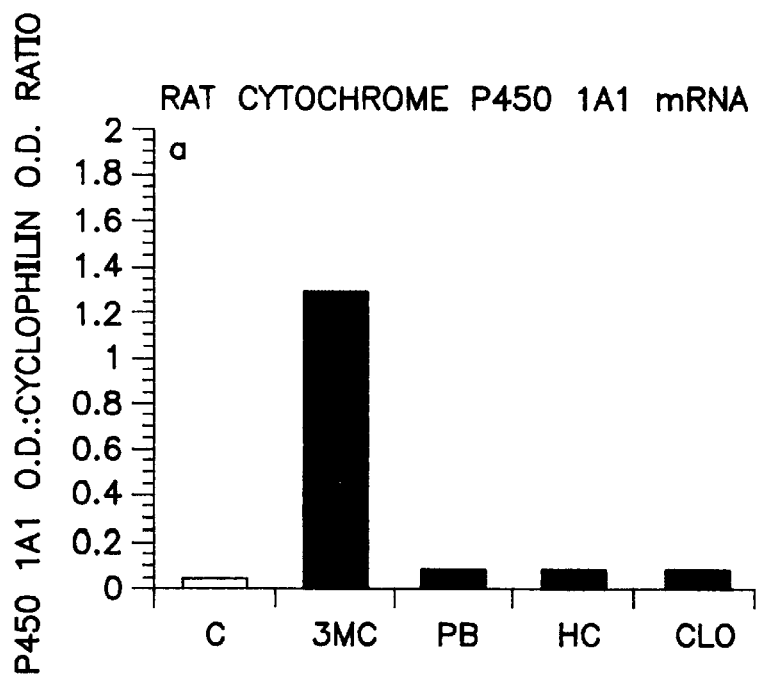
Figures 1, 3B:
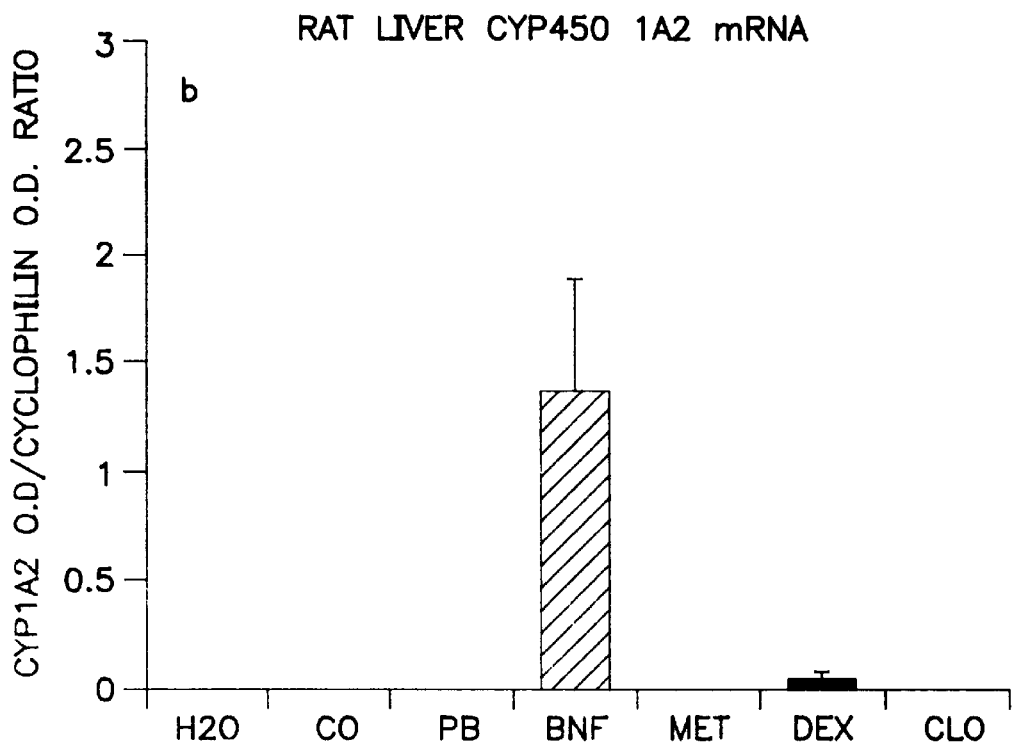
Figures 2, 3B:
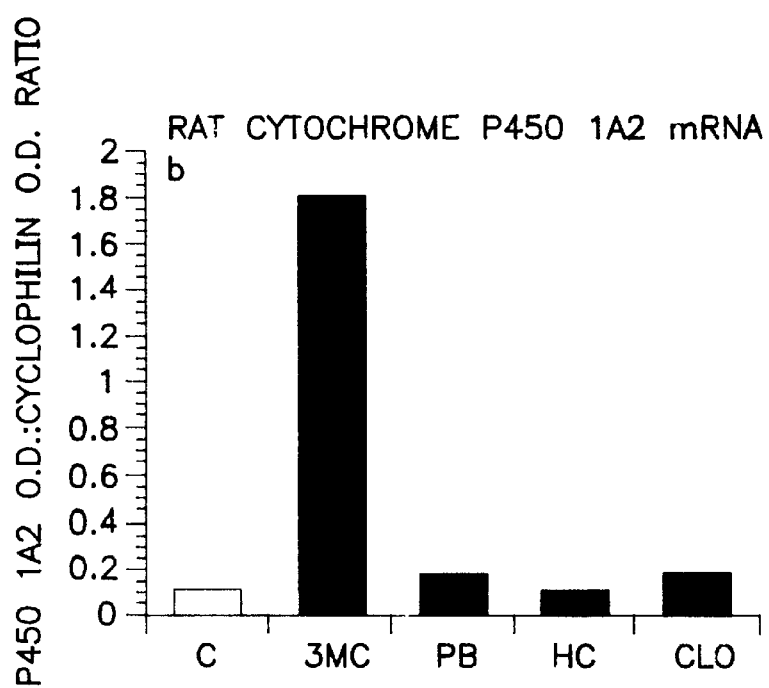
Figures 1, 3C:
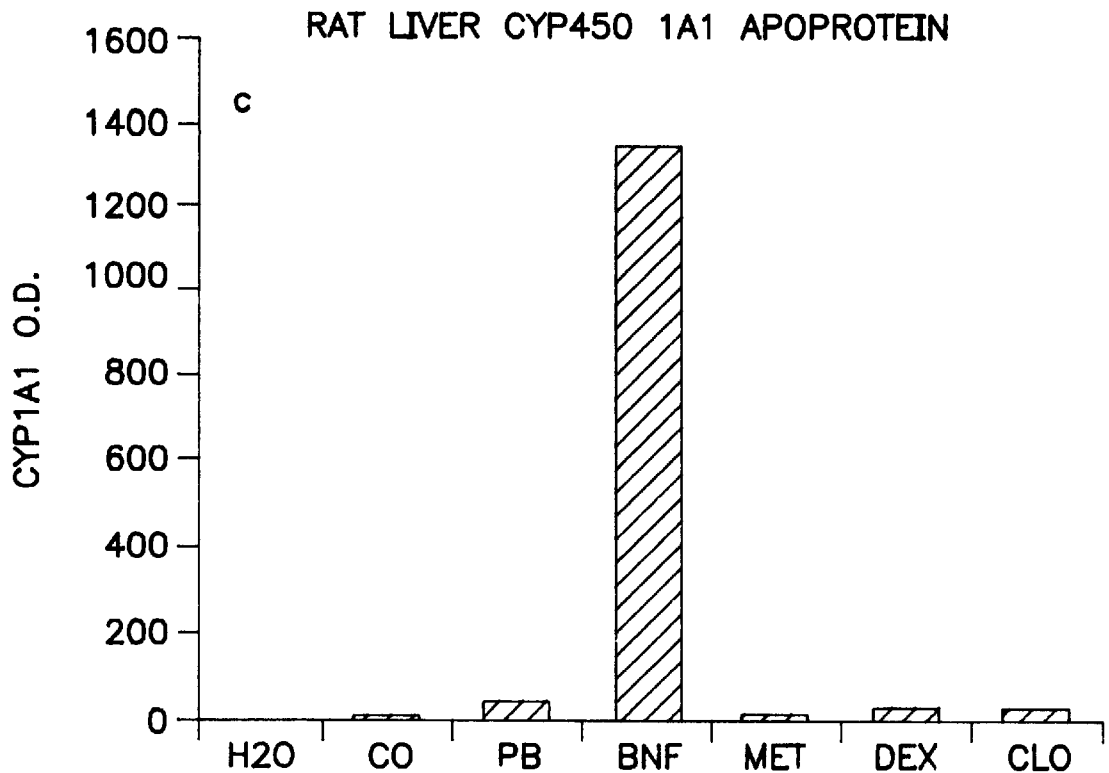
Figures 2, 3C:
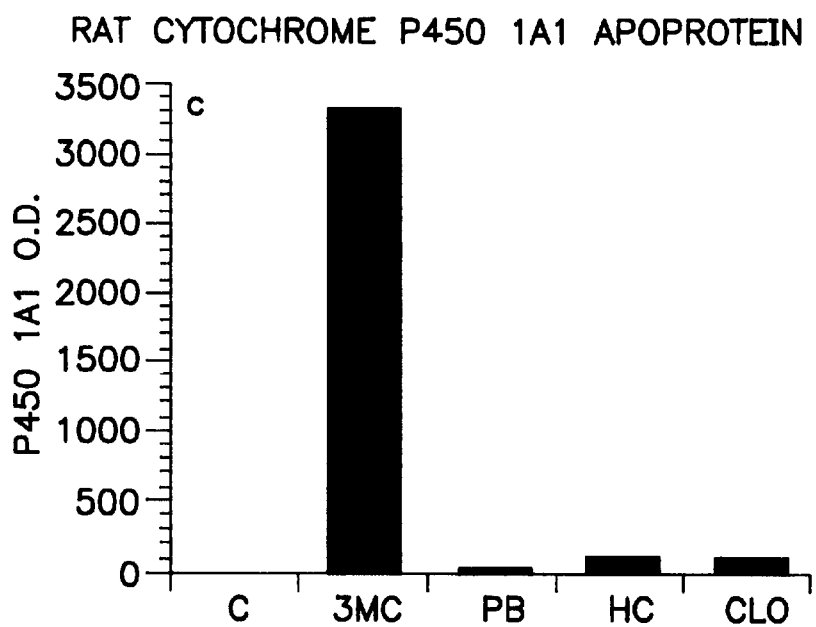
Figure 3D:
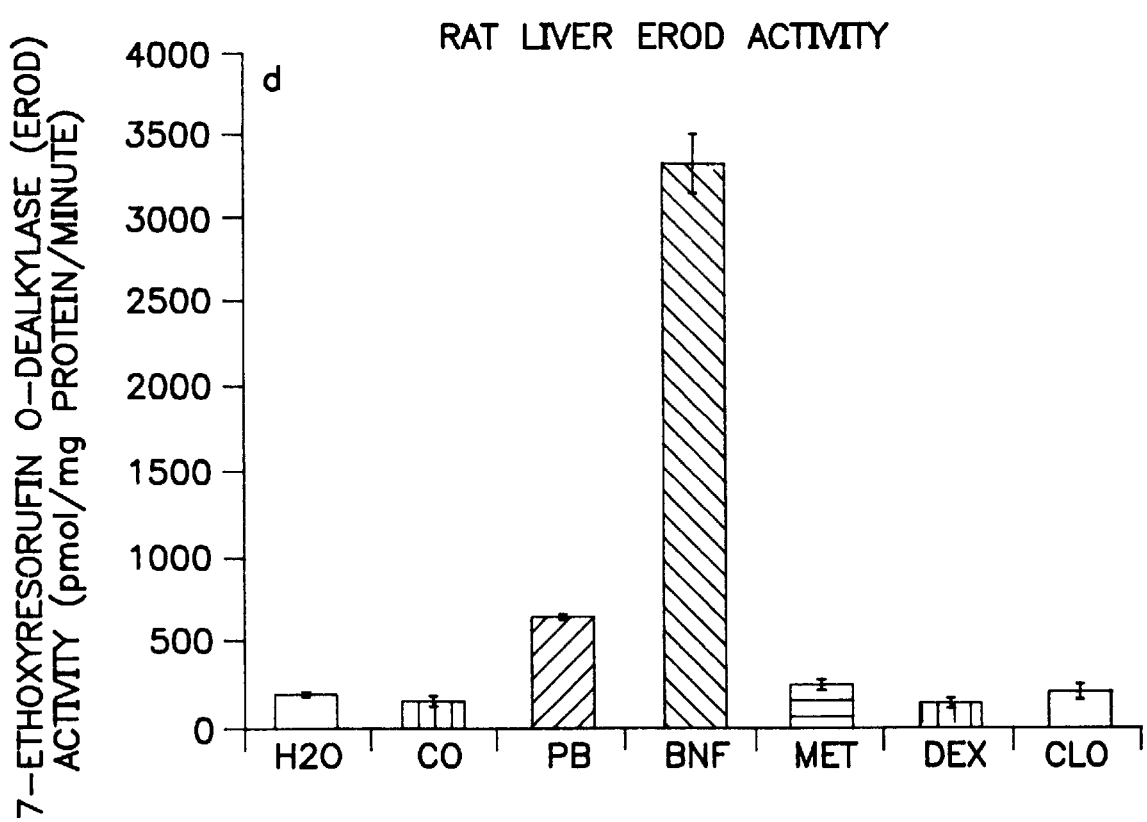
Figures 1, 3E:
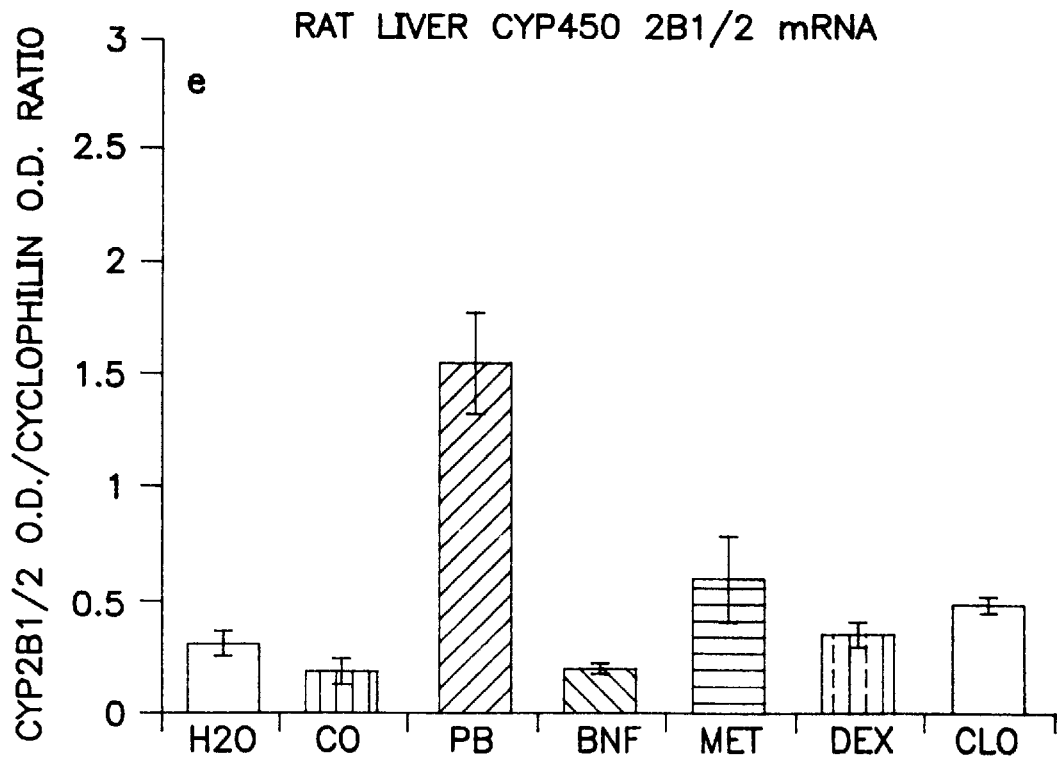
Figures 2, 3E:
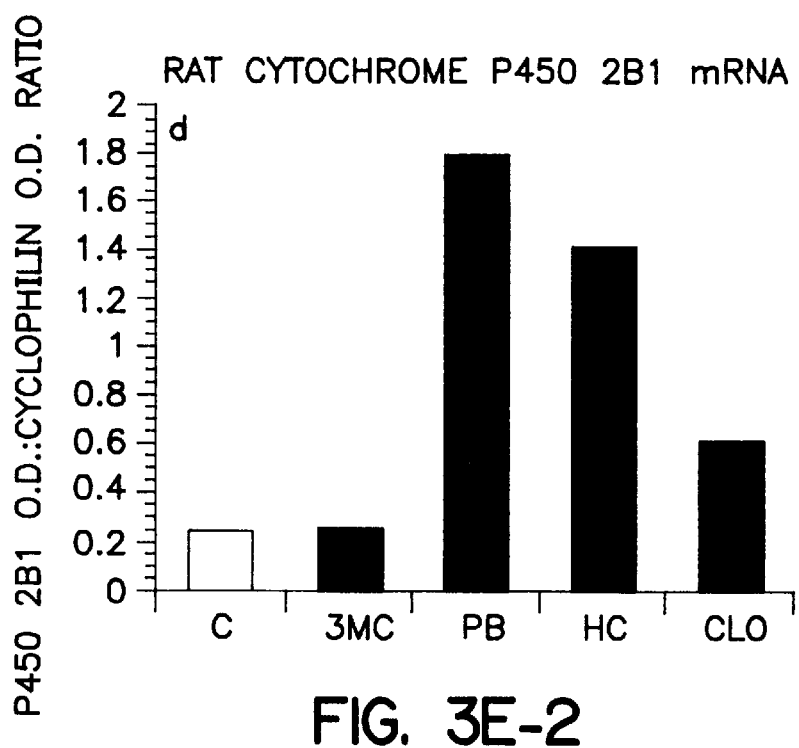
Figures 1, 3F:
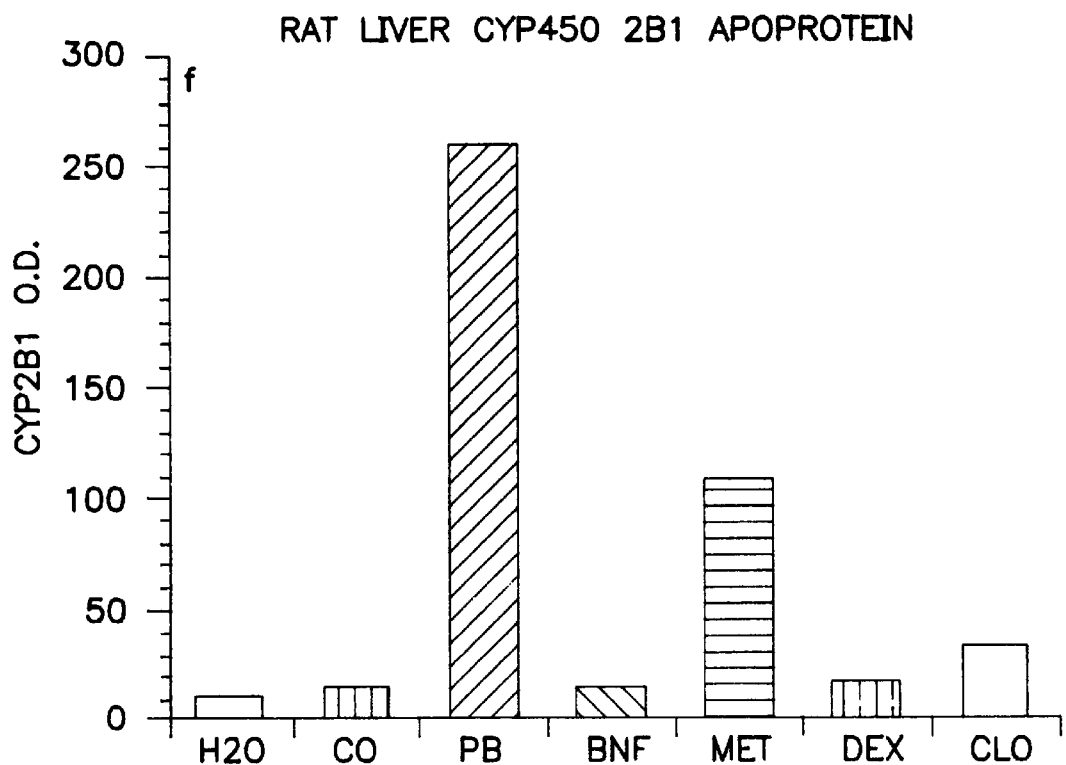
Figures 2, 3F:
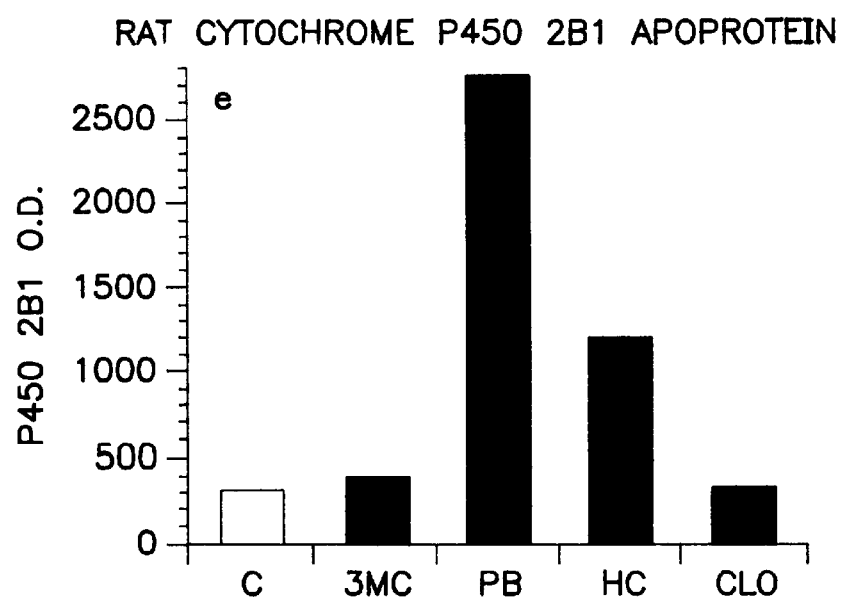
Figure 3G:
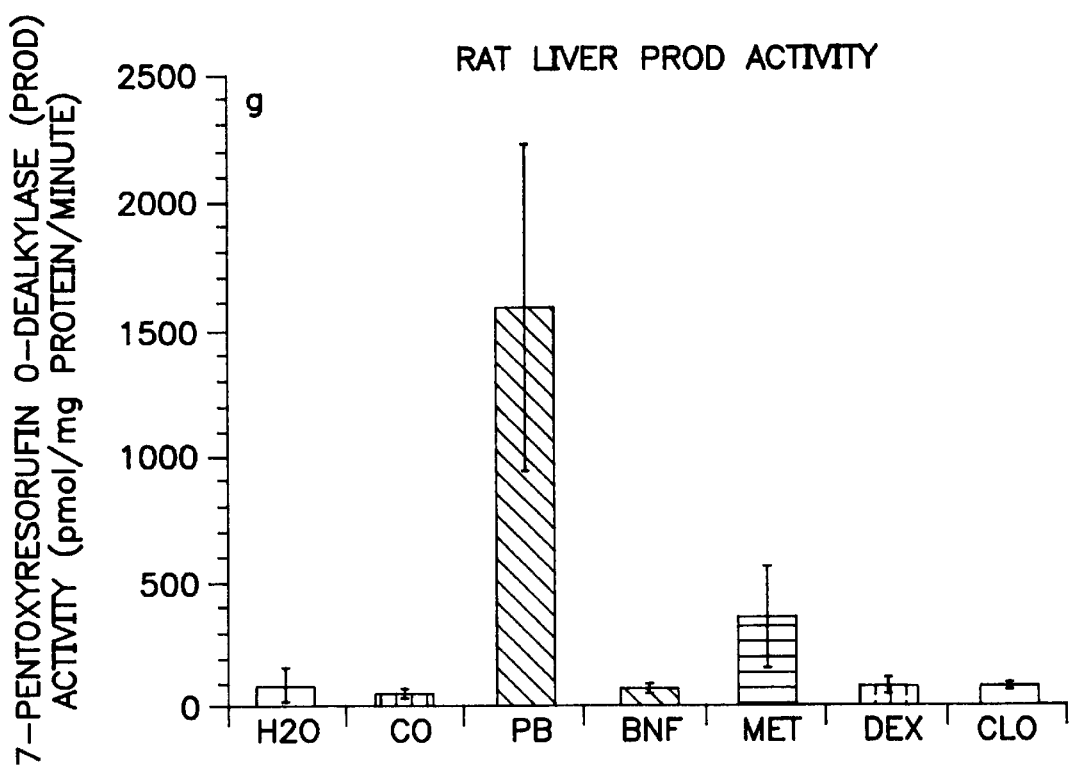
Figure 3H:
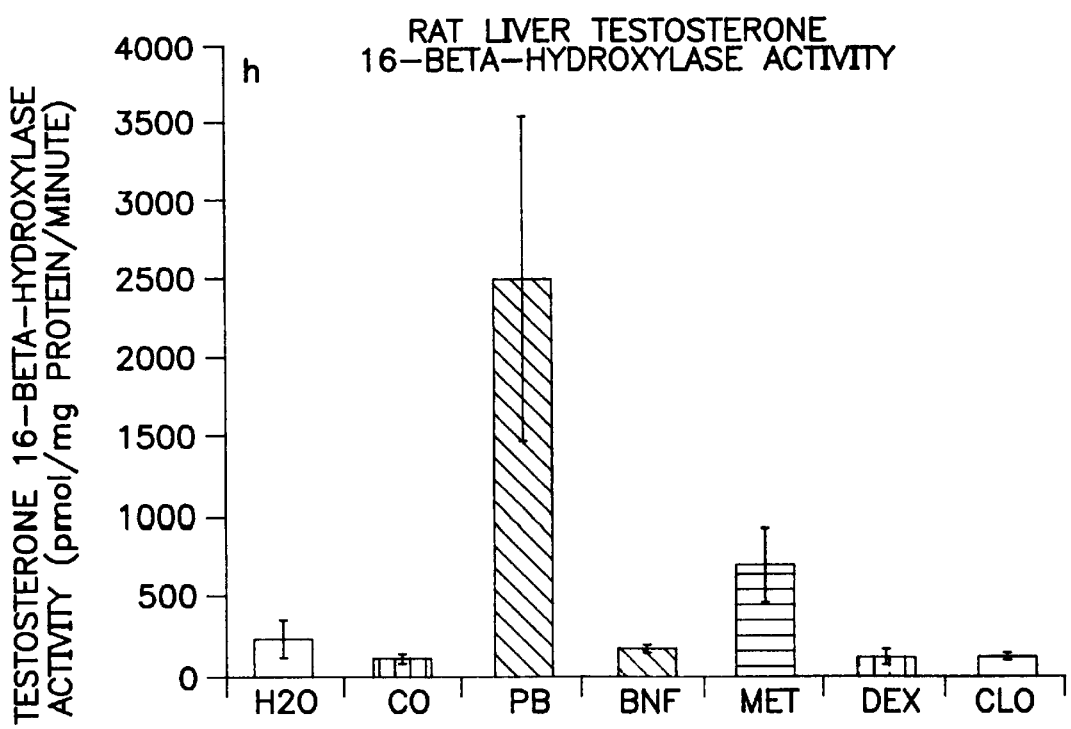
Figures 1, 3I:
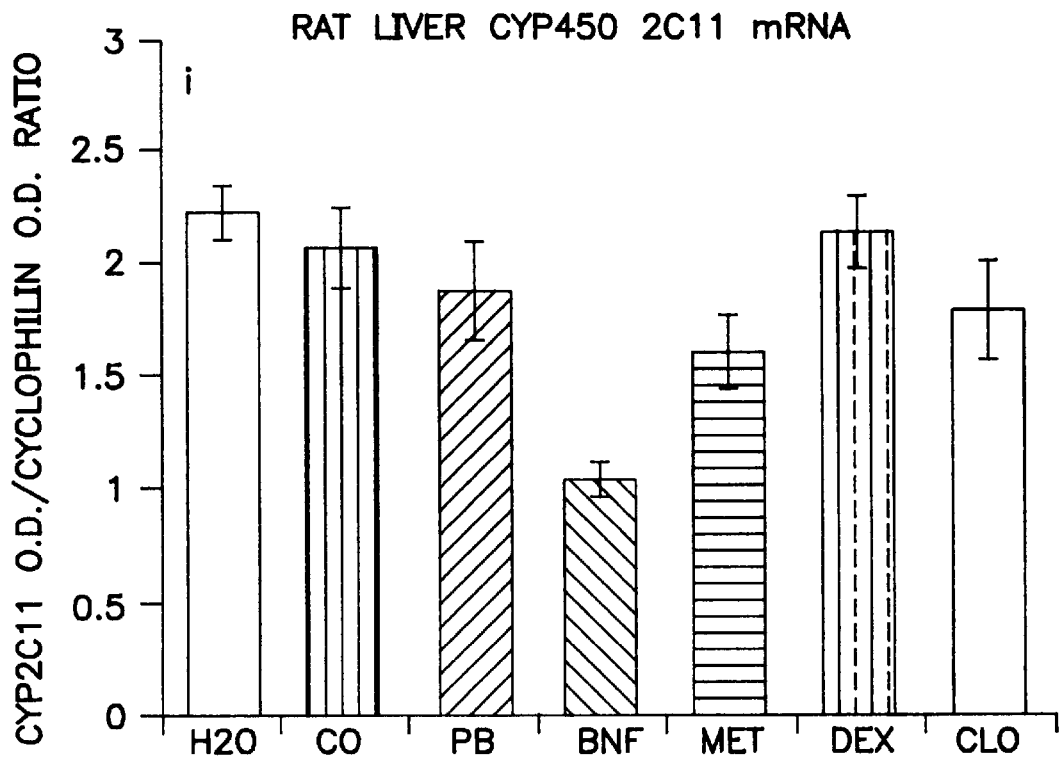
Figures 2, 3I:
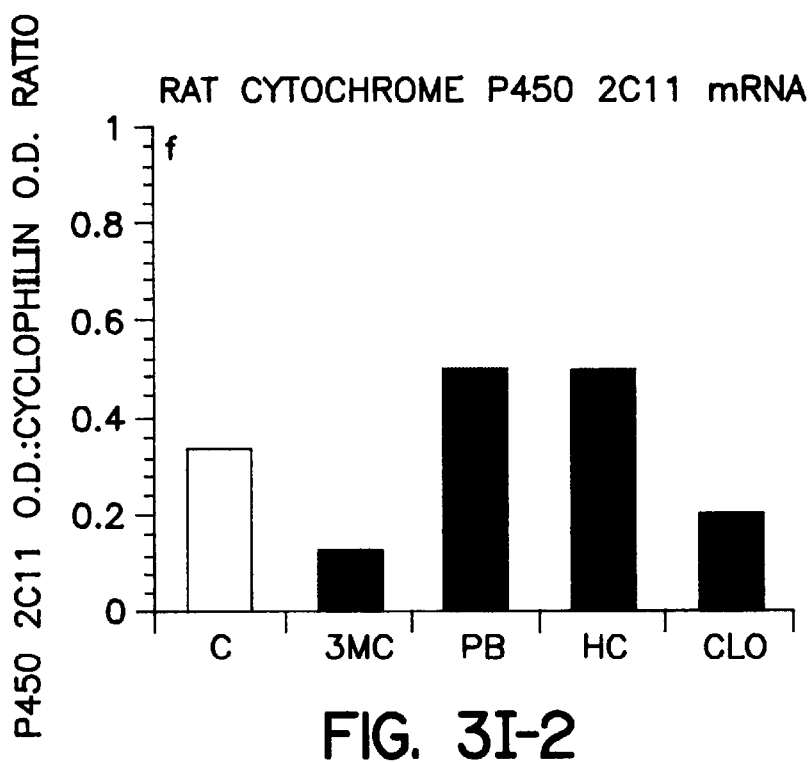
Figures 1, 3J:
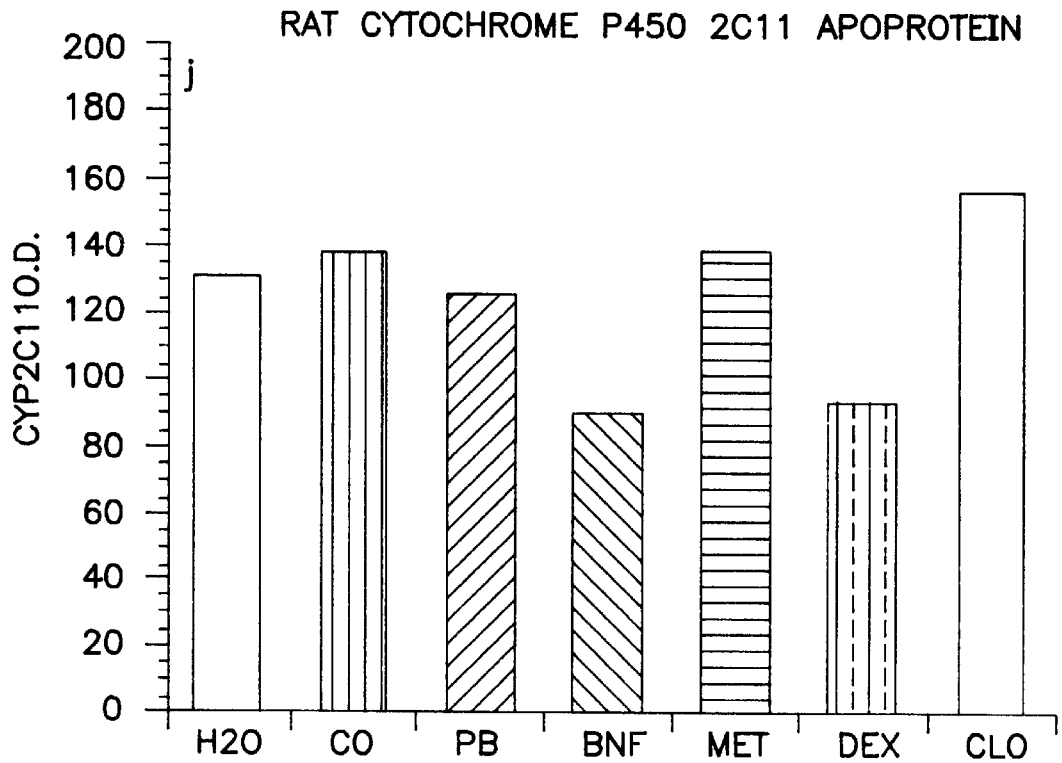
Figures 2, 3J:
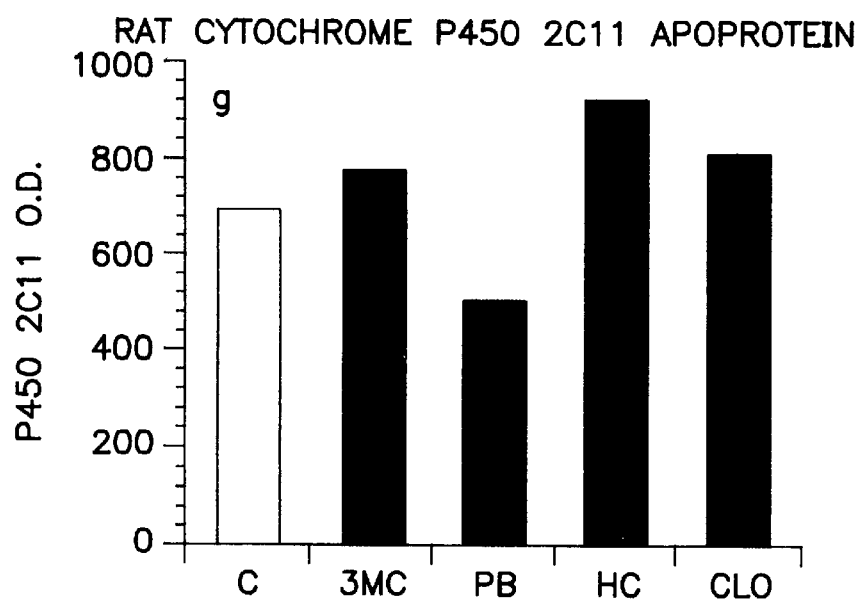
Figure 3K:
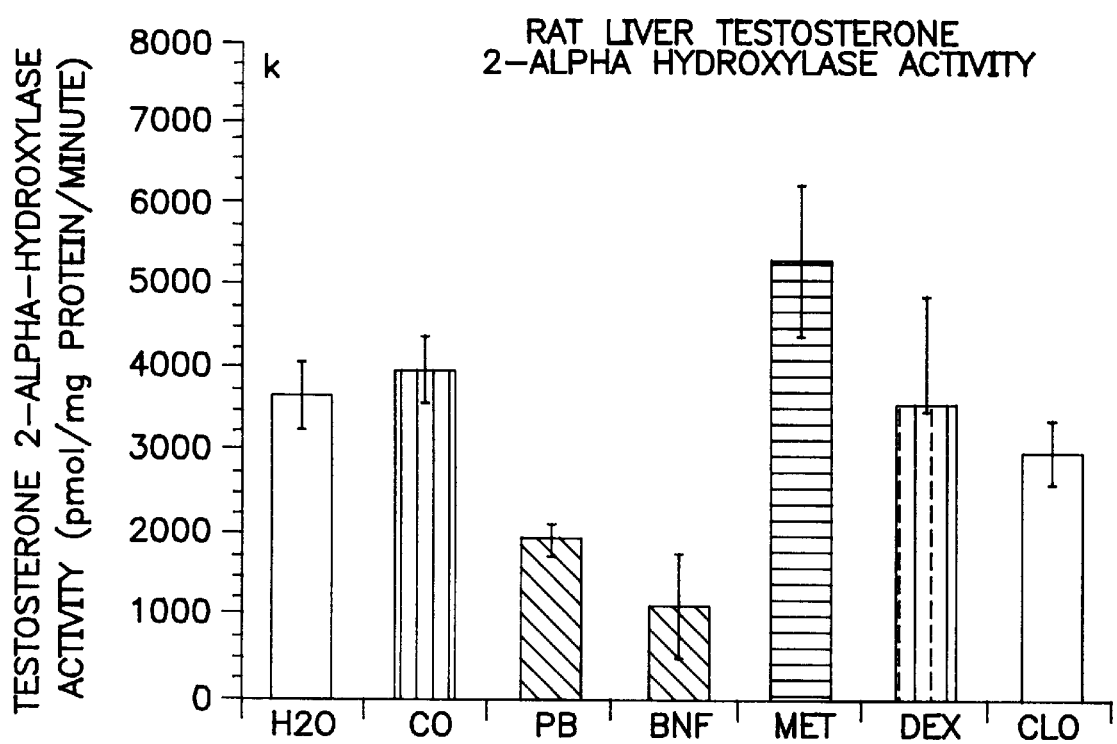
Figures 1, 3L:
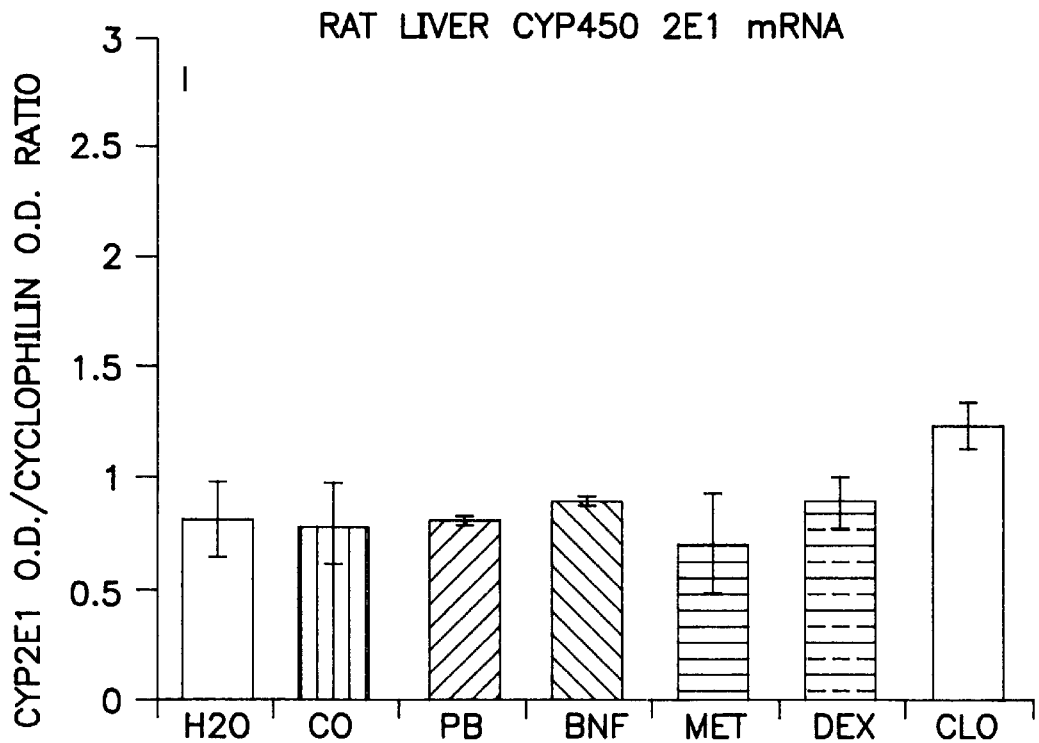
Figures 2, 3L:
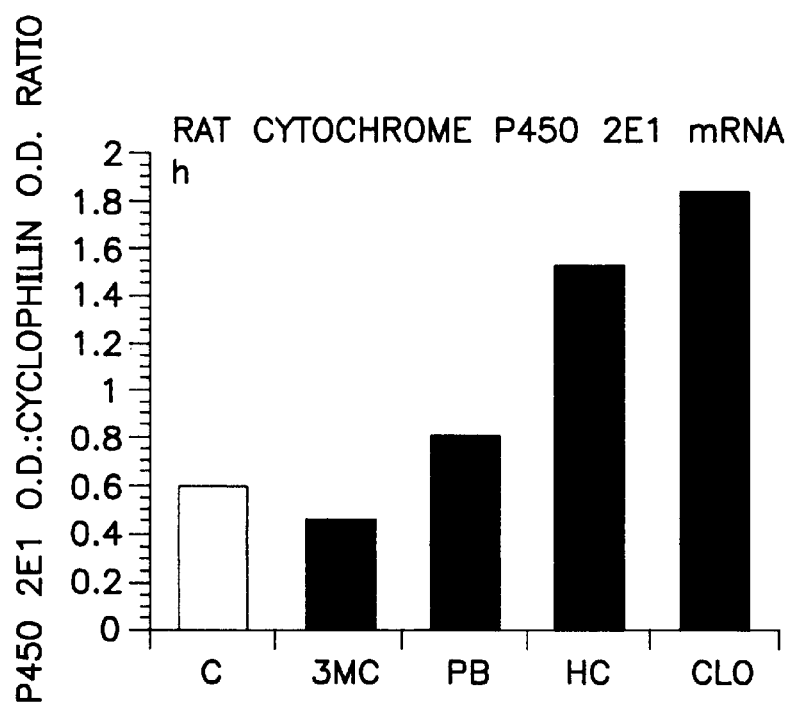
Figures 1, 3M:
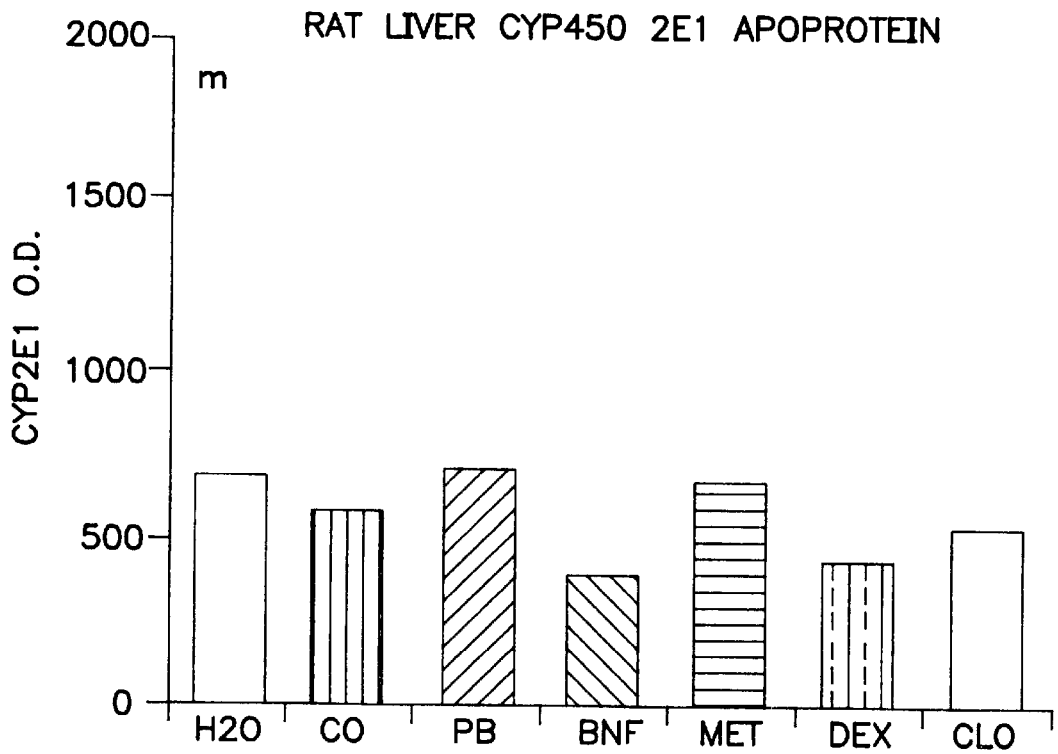
Figures 2, 3M:
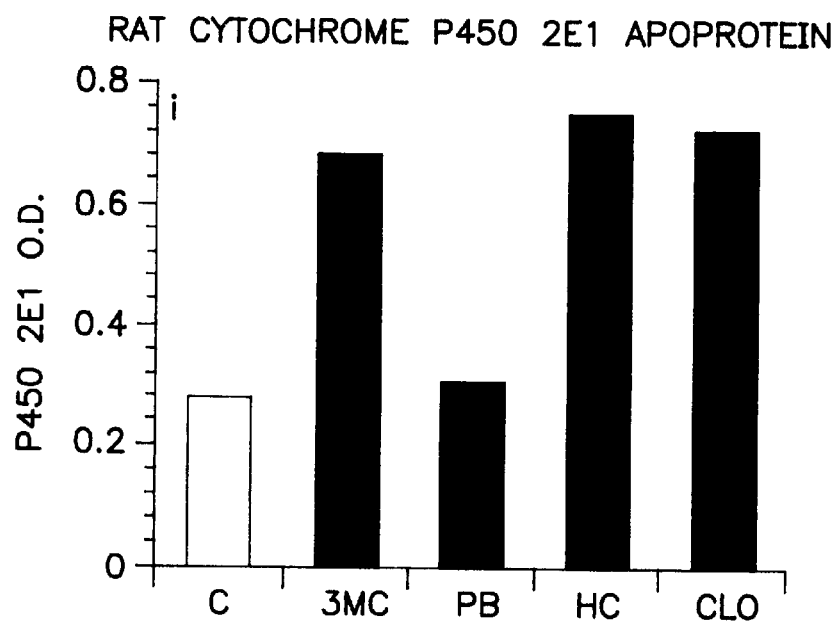
Figure 3N:
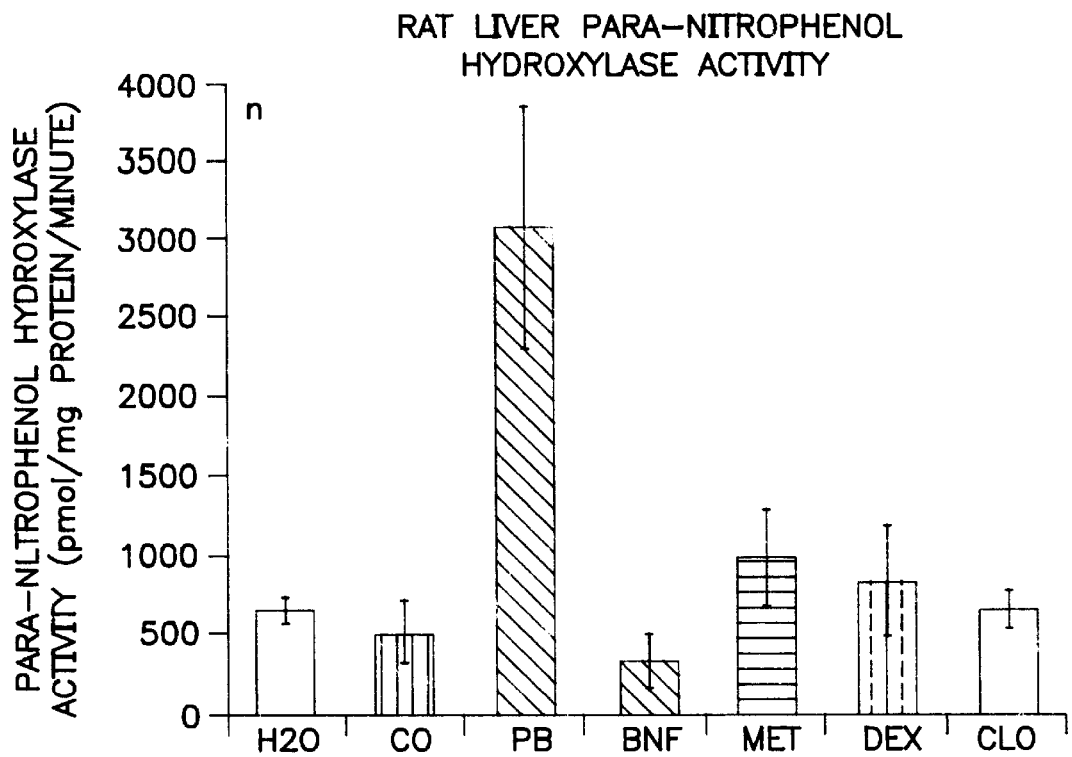
Figure 3O:
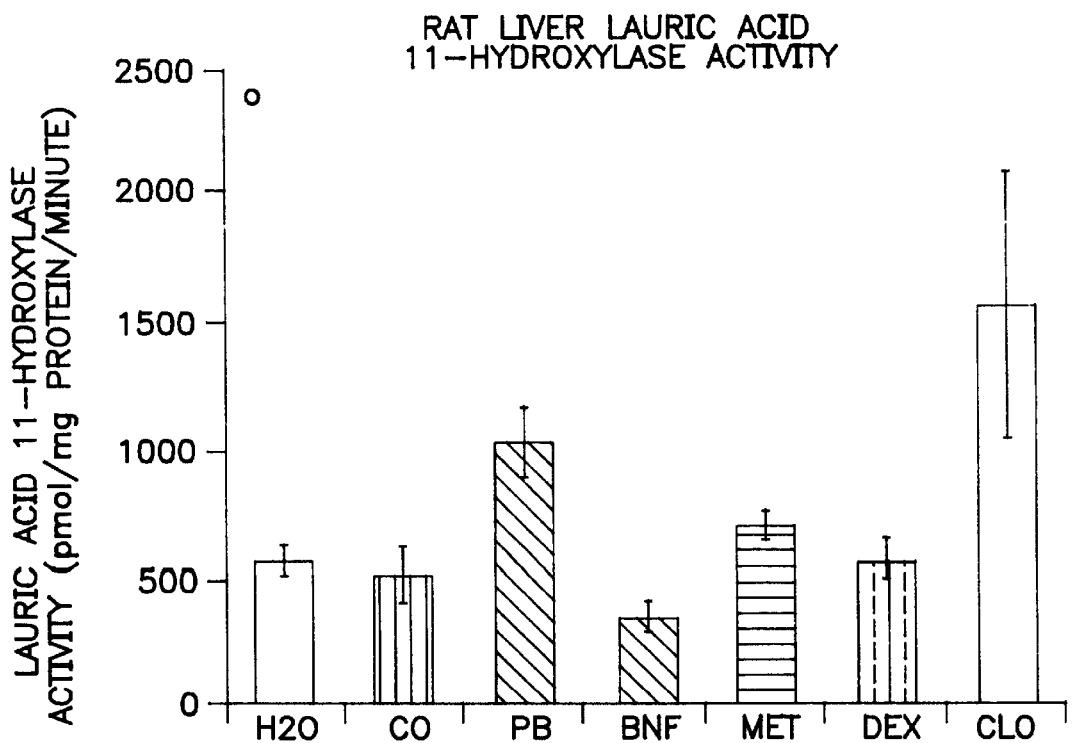
Figure 3P:
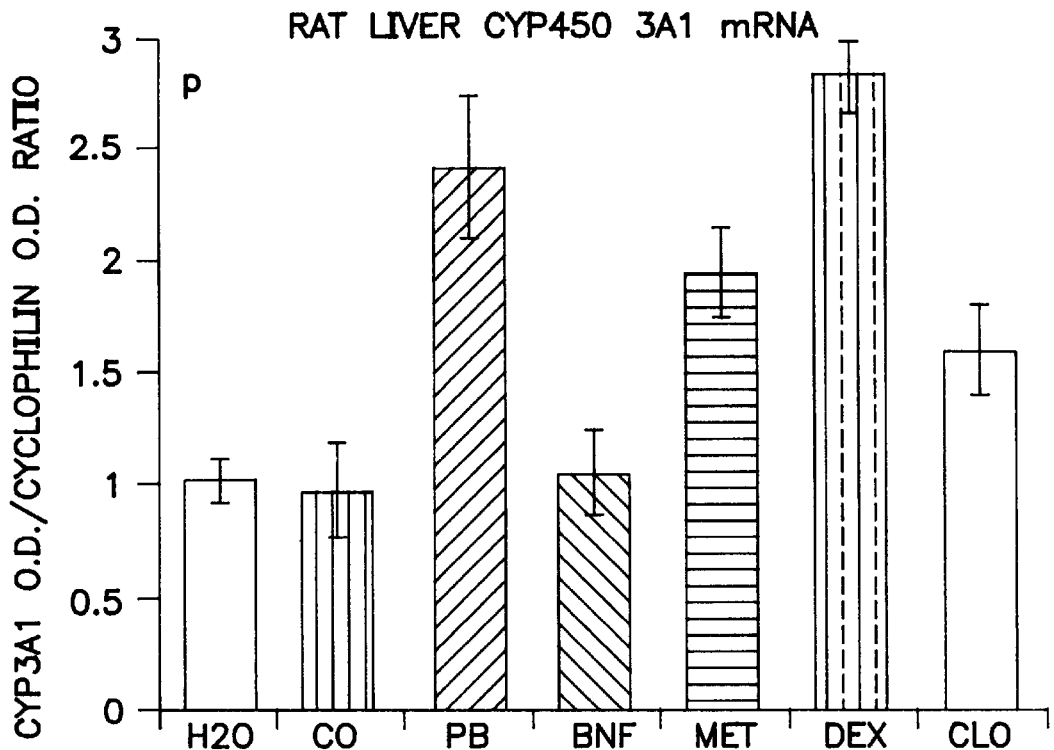
Figure 2:
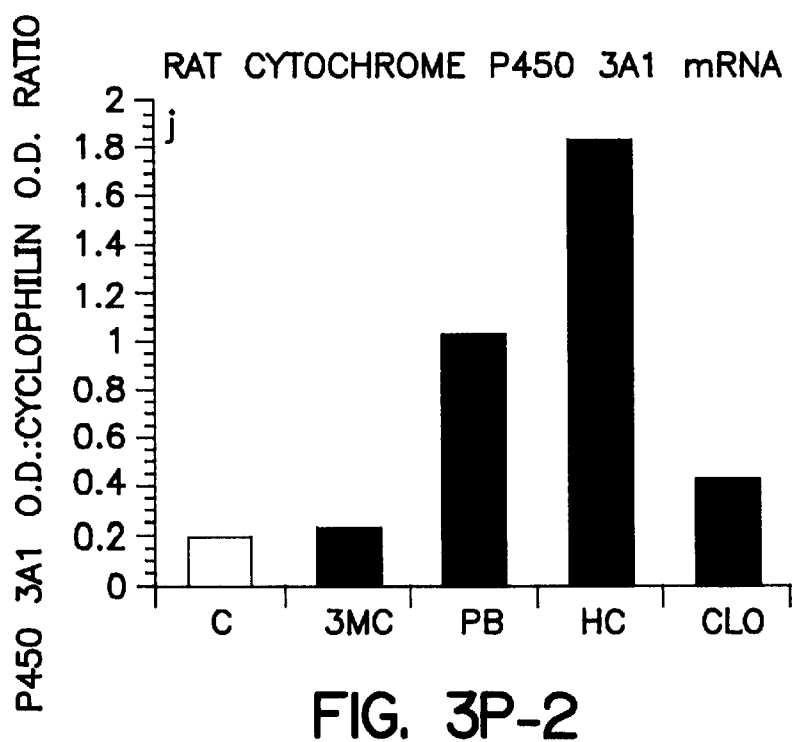
Figures 1, 3Q:
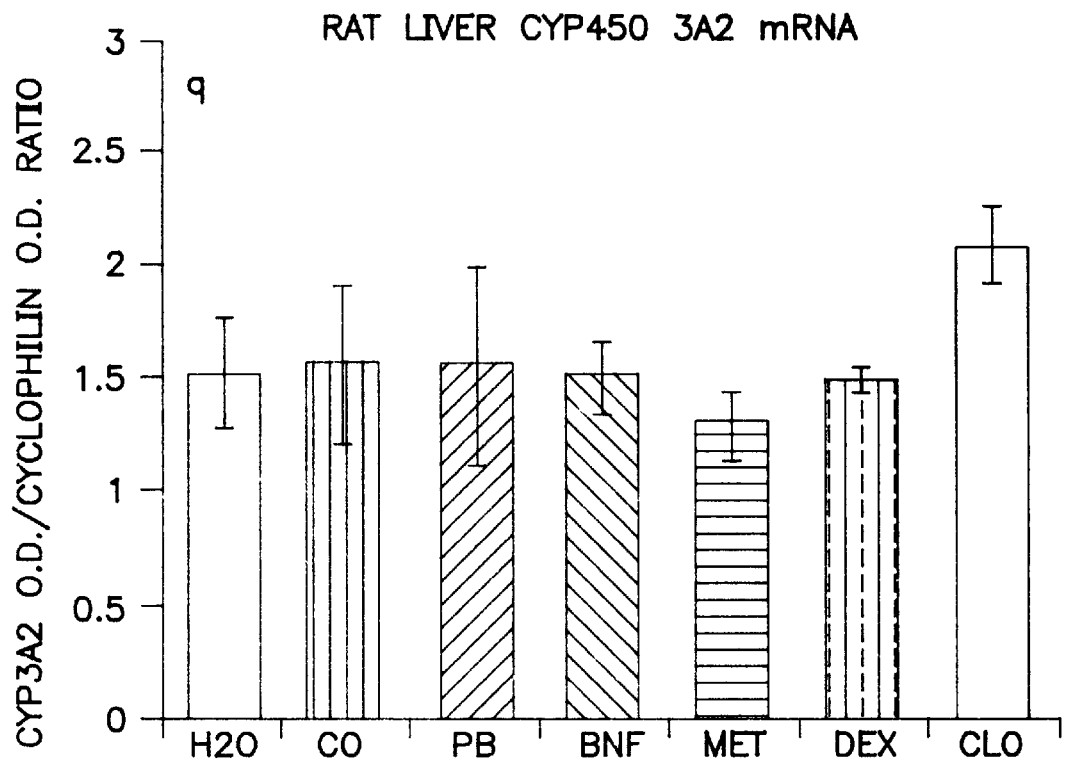
Figures 2, 3Q:
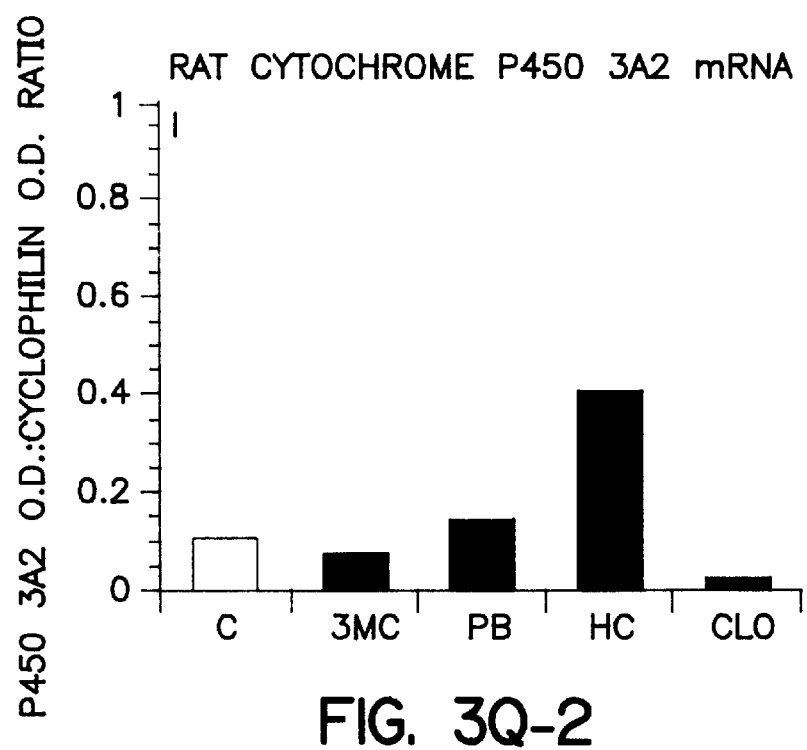
Figures 1, 3R:
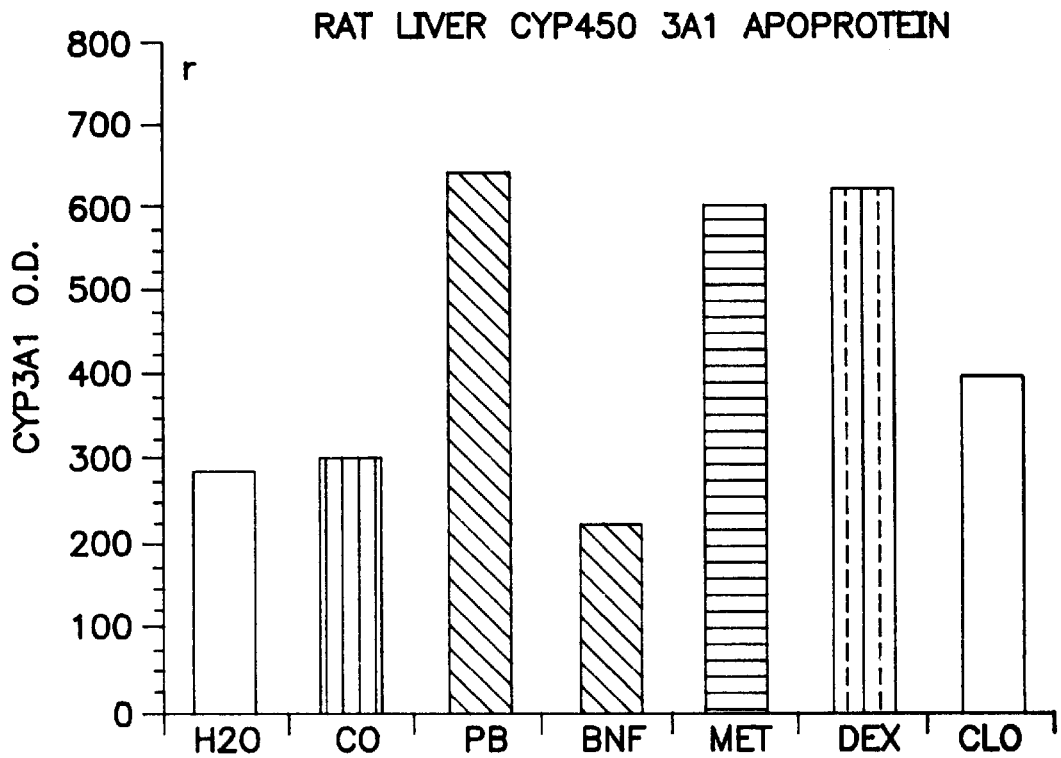
Figures 2, 3R:
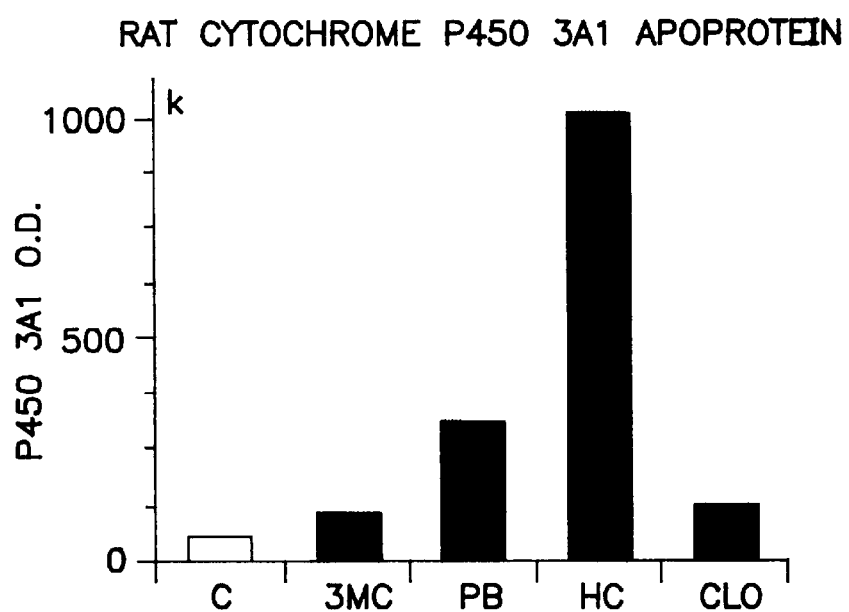
Figure 3S:
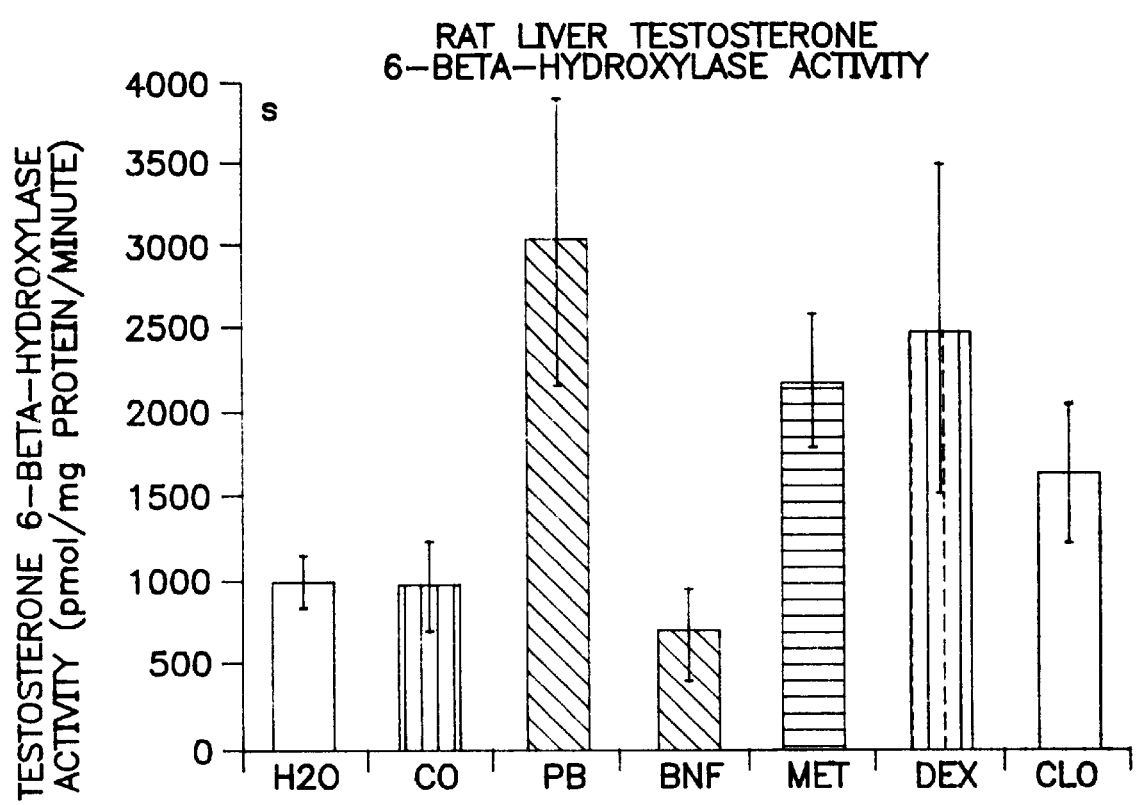
Figure 3T:
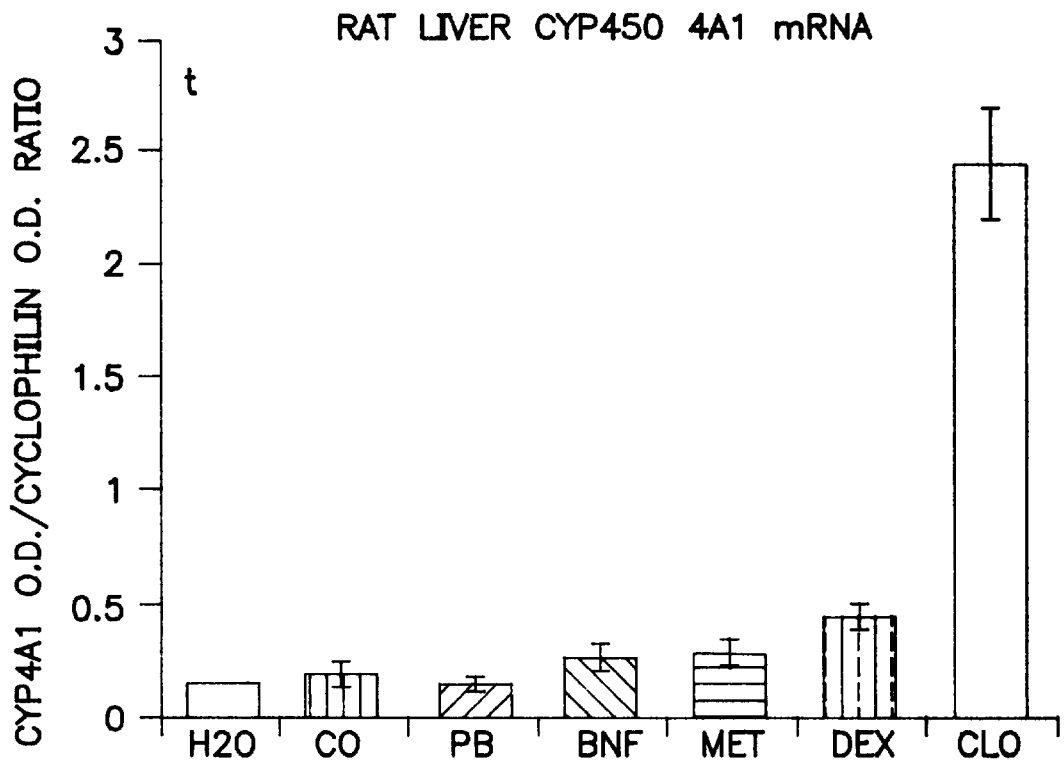
Figure 2:
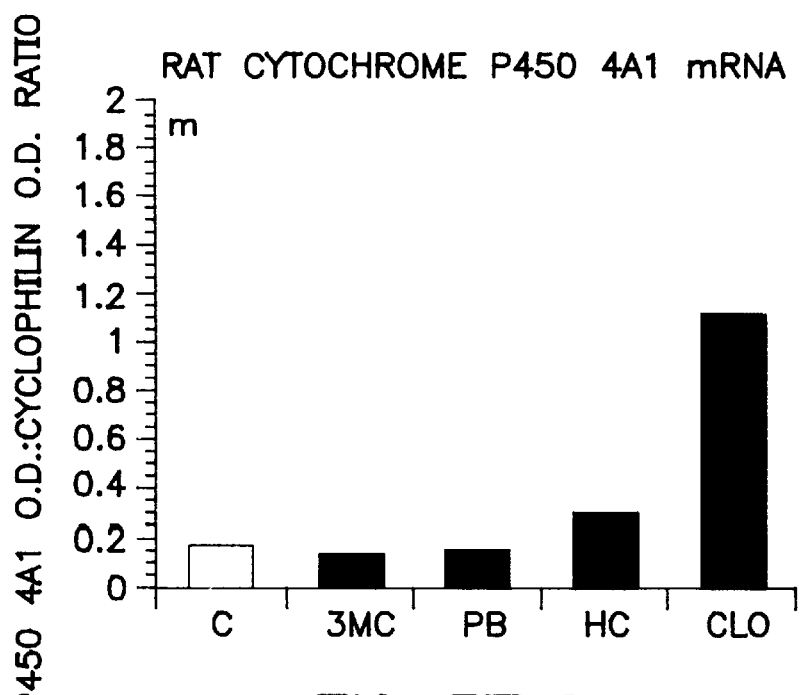
Figures 1, 3U:
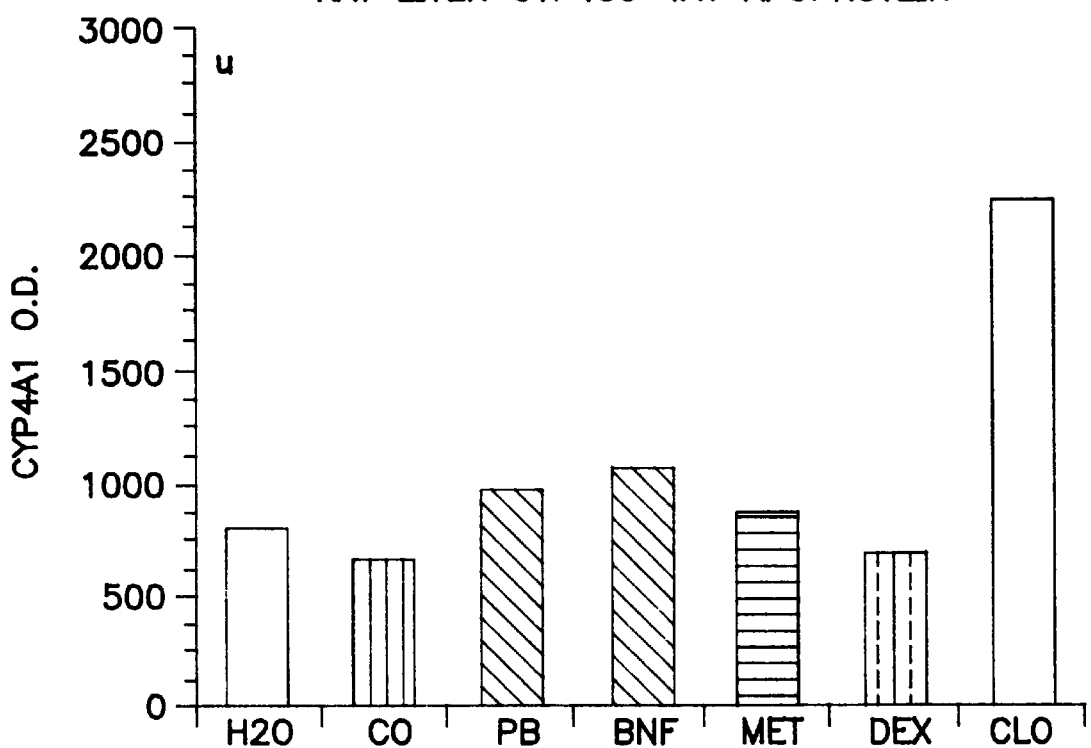
Figures 2, 3U:
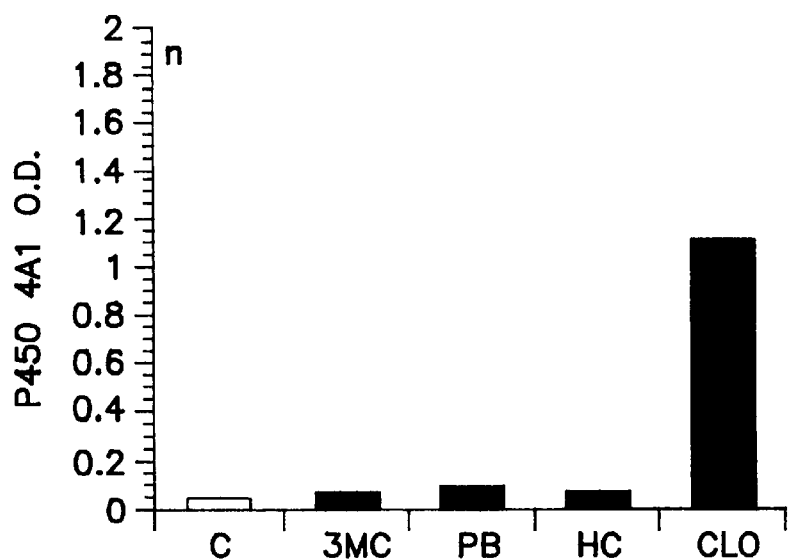
Figure 3V:
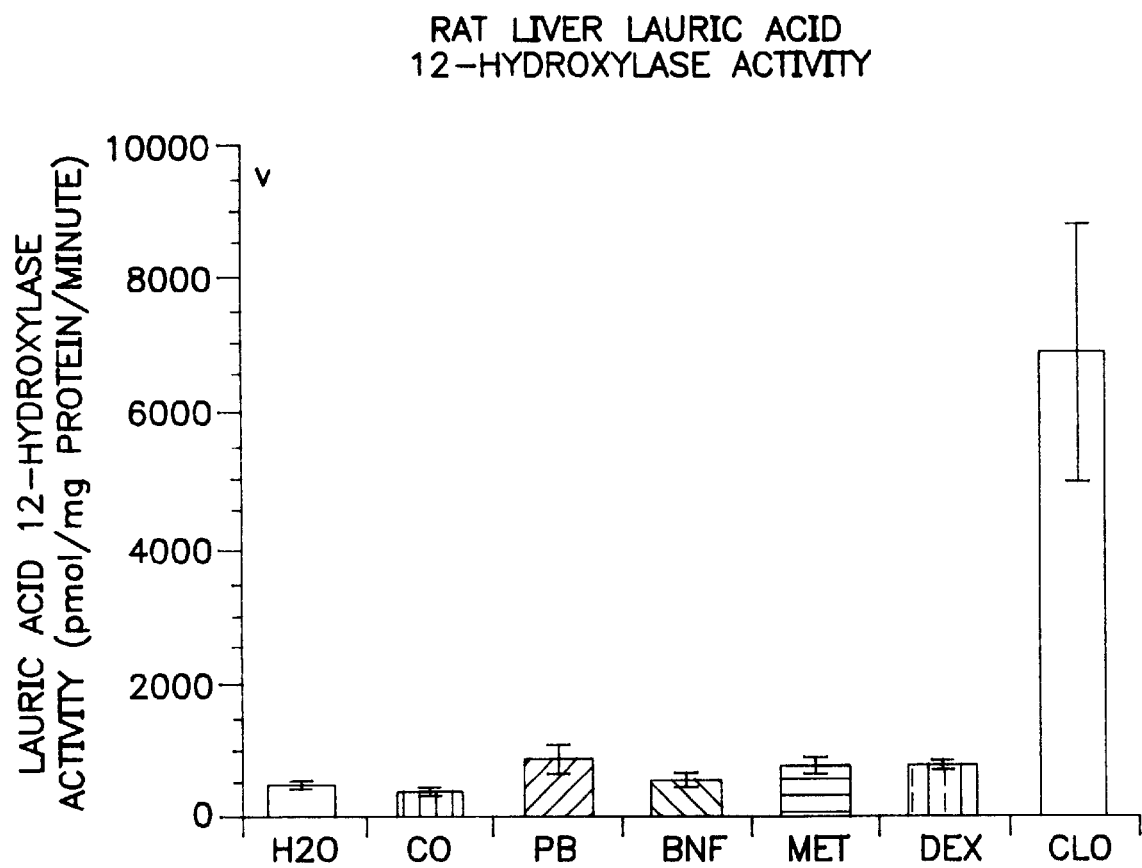
Figures 1, 3W:
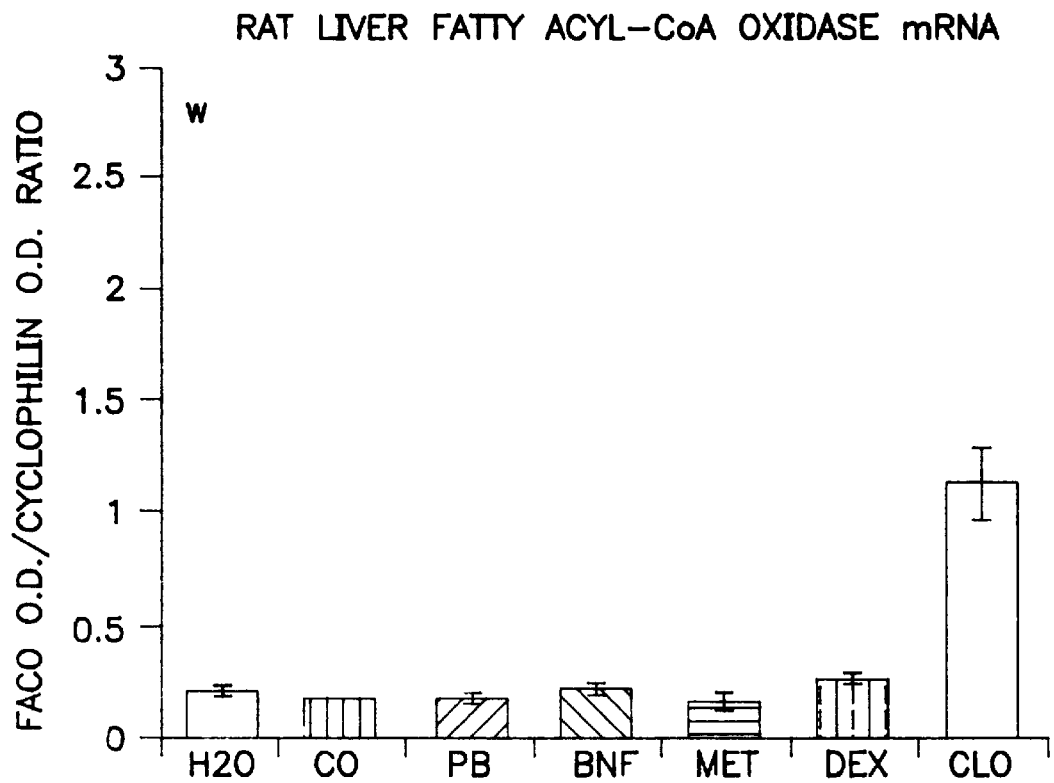
Figures 2, 3W:
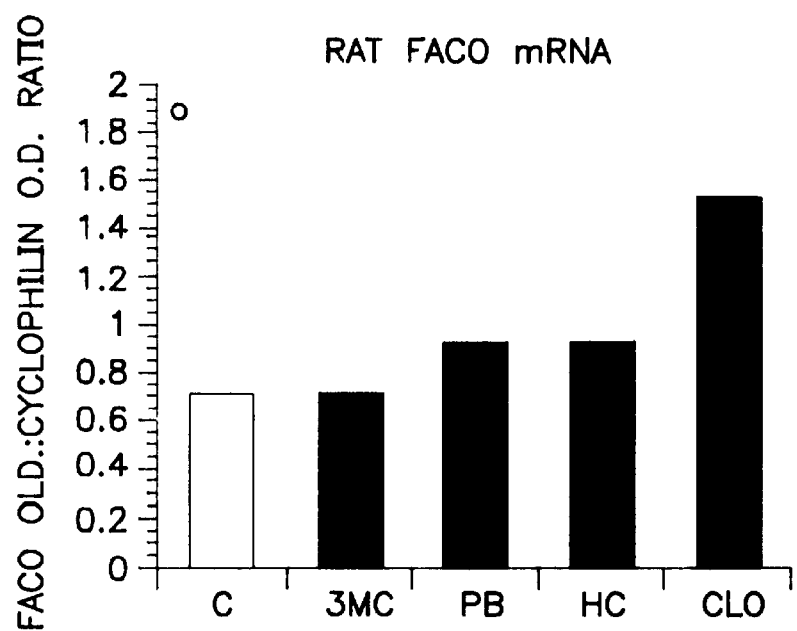
Figure 3X:
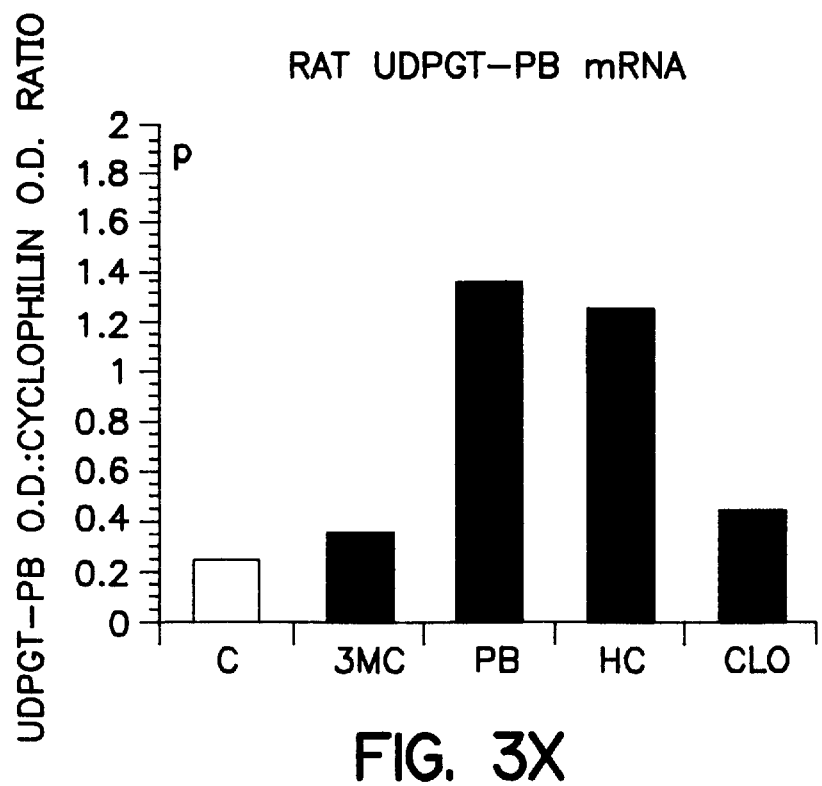
Figure 3Y:
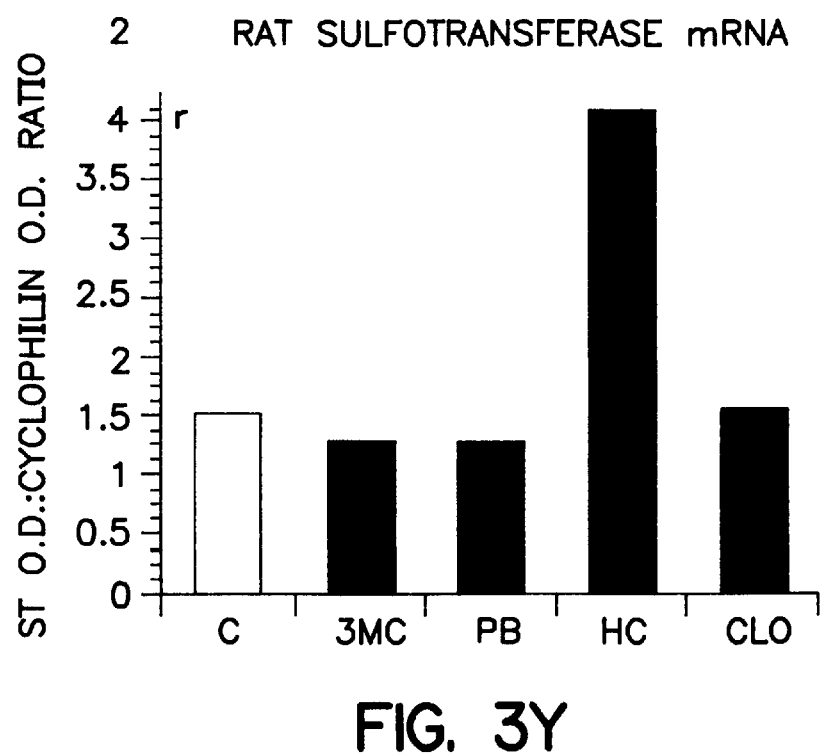
Figure 3Z:
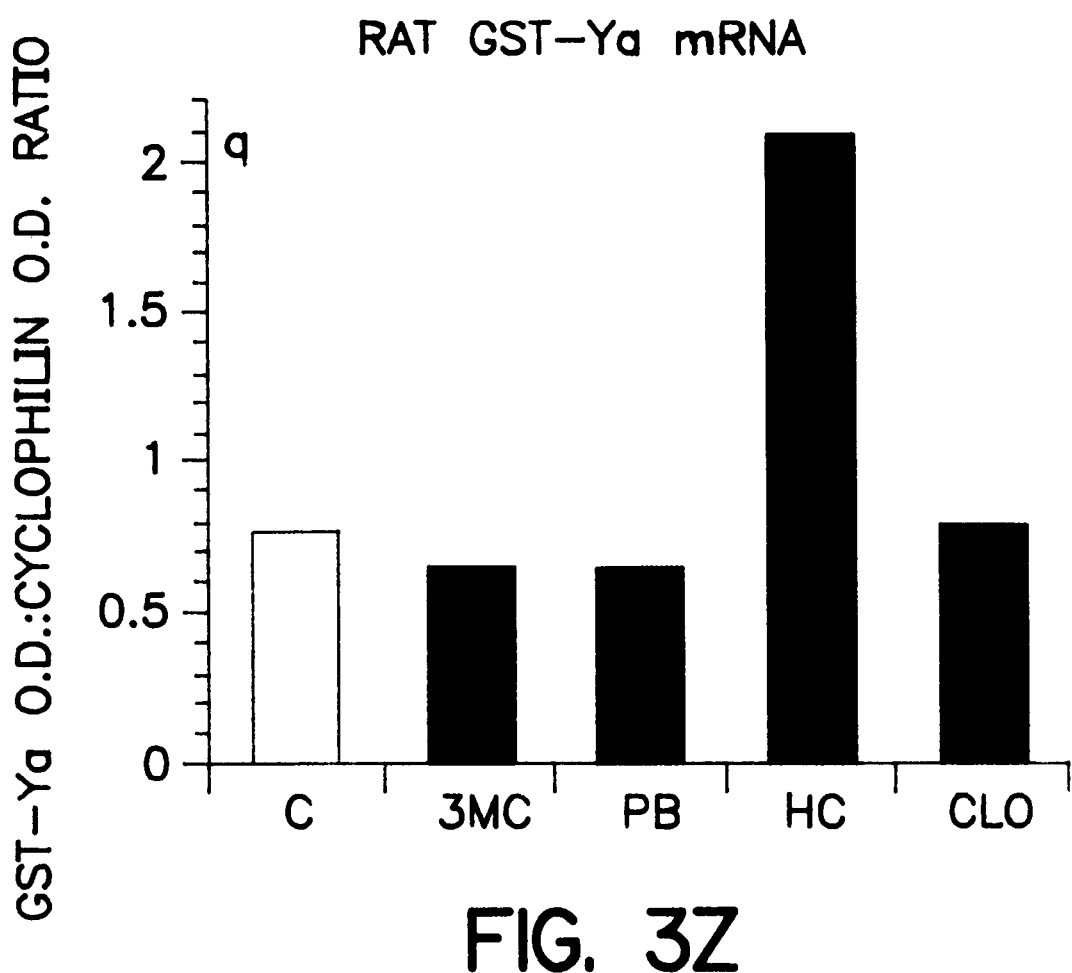

As shown in FIGS. 3a–3w, all experiments showed correlation between the expression of CYP450 enzymes at the mRNA and protein levels. These results indicate that CYP450 enzyme expression in general is regulated primarily at the mRNA level. This is particularly evident in cases where certain of the compounds tested (e.g., BNF) were found to markedly reduce CYP450 mRNA and apoprotein expression and enzyme activity. (Expression of the CYP2E1 isoenzyme, which is generally increased via protein stabilization, is an exception to this mechanism of CYP450 enzyme regulation.) Additionally, for most of the CYP450 enzymes (i.e., CYP450 1A1, 2B1/2, 3A1 and 4A1), expression of mRNA and apoprotein correlated with enzymatic activity against selective substances. Minor differences were identified only for the CYP2C11 and CYP2E1 isoenzymes, where the enzymatic substrates are known to be less specific.

Treatment of rats with BNF was found to cause increases in the expression of both CYP1A1 and CYP1A2 mRNA, CYP1A1 apoprotein and corresponding EROD activity. PB was also found to cause a slight increase in both CYP1A1 apoprotein and EROD activity, but not in either CYP1A1 or CYP1A2 mRNA.

Treatment of rats with BNF was also found to cause a marked decrease in the expression of the male specific CYP450 isoenzyme, 2C11. This effect has been observed using a number of aromatic hydrocarbons and is related to an effect on the pituitary release of growth hormone and subsequent suppression of androgen production, a phenomena often termed as the "feminization" of CYP450 expression. This effect was particularly prominent at the mRNA expression level. Thus, the PT-PCR technique can be used to assess the potential effects of xenobiotics on endocrine function.

PB treatment resulted in the prototypical increase in CYP2B and CYP3A1 expression. CYP3A2 was not induced by PB in these studies; this effect has been reported, Gonzales, et al., *Mol. Cell. Bio.* 6: 2969–2976, 1986. MET was also found to be an inducer of the CYP2B and CYP3A1 enzymes. These findings indicate that inhibitors of CYP450 enzyme activity have no readily detectable effect on their capacity to cause enzyme induction at either the mRNA or apoprotein levels.

Dexamethasone treatment caused a prototypical pattern of CYP450 expression in rat liver, resulting in a selective increase in the expression of CYP3A1. As in the case of PB, DEX did not induce the expression of the CYP3A2 enzyme, demonstrating that these two isoenzymes of CYP450 are differentially regulated in the rat liver.

The hypolipidemic agent, CLO, was found to be a broad spectrum inducer of CYP450 in the rat liver, inducing an increase in the expression of CYP450 3A1, 3A2, 4A1 and FACO using all three methods of detection. These findings demonstrate that in addition to peroxisome proliferator activity, CLO causes an increase in the expression of multiple CYP450 enzymes. Moreover, CLO was found to consistently induce the expression of CYP2E1 at both the mRNA and apoprotein levels in our studies.

mRNA expression as measured by RT-PCR can be used to accurately monitor the changes in expression of most CYP450 isoenzymes in rat liver following exposure to xenobiotics. Given the advantages of selectivity, sensitivity and speed of this versus traditional methods, these studies demonstrate the utility of RT-PCR for analysis of CYP450 expression in the rat during routine toxicology studies.

EXAMPLE 1

(Application to an In Vivo Test System)

Male Sprague-Dawley rats between the ages of 6–8 weeks and weighing 200–300 g were used in these studies. Food and water were available ad libitum.

Animals were administered either phenobarbital (PB) (100 mg/Kg), β-napthoflavone (BNF) (100 mg/Kg), isoniazid (INH) (200 mg/Kg), metyrapone (MET) (100 mg/Kg, dexamethasone (DEX) (200 mg/Kg) or clofibrate (CLO) (250 mg/Kg) for 4 consecutive days via intraperitoneal (i.p.) injection. Animals treated with water ($H_2O$) and corn oil (CO) were used as controls. Two hours following the last injection (day 4), animals were sacrificed and the livers removed. The livers were immediately frozen and stored at −70° C.

Preparation of Total Liver RNA

Total RNA was prepared from frozen liver tissue using a modification of the method described by Xie and Rothblum, *Biotechniques* 11:326–327, 1991. Approximately 100–200 mg. of liver tissue was homogenized in RNA extraction buffer to isolate total RNA. The resulting RNA was reconstituted in diethylpyrocarbonate-treated water (DEPC-$H_2O$), quantitated spectrophotometrically at 260 nm and adjusted to 100 μg/ml. Total RNA was stored in DEPC-$H_2O$ at −70° C. without any apparent degradation.

Reverse Transcriptase-Polymerase Chain Reaction (RT-PCR)

For conversion of total RNA to cDNA, a 20 μl reaction mix was prepared containing 1× reverse transcriptase (RT) buffer (GIBCO BRL), 10 nM DTT (dithiothreitol) 0.5 nM dTPs (deoxynucleotide triphosphates), 2.5 μM oligo d(T)$_{15}$ primer, 40 units RNasin, 200 units RNase H-RT (GIBCO BRL) and 400 ng of total RNA (in DEPC-$H_2O$). The reaction was incubated for 1 hour at 37° C. followed by inactivation of the enzyme at 95° C. for 5 minutes. cDNA was stored at −20° C. until use.

For the PCR amplification of cDNA, a 10 μl reaction mix was prepared containing 10× polymerase reaction buffer, 2 mM $MgCl_2$, 1 unit Taq DNA polymerase, 20 ng cDNA and 200 nM of the 5' and 3' specific PCR primers. PCR reactions were carried out using melting, annealing and extension cycling conditions of 94° C. for 30 seconds, 56° C. for 1 minute and 72° C. for 1 minute. All amplifications were carried out for 23 cycles. Under these conditions, all cDNA fragment amplifications were found to produce single products within a linear range of 20–26 cycles. Amplified cDNA products were separated by PAGE (polyacrylamide gel electrophoresis) using 5% native gels. Gels were stained with ethidium bromide and photographed on a transilluminator using Polaroid positive/negative film. The amount of each product was quantitated densitometrically using a scanning laser densitometer.

Preparation of Liver Microsomes

Liver microsomes were prepared from frozen livers as described in Cheng et al., *J. Biol. Chem.* 259: 12279–12284, 1984. Microsomes were resuspended in buffer containing 10 mM Tris-HCl, 1 mM EDTA, and 20% glycerol. Microsomes were snap frozen in liquid nitrogen and stored at −80° C. until use. Total protein was measured using the bicinchonic acid (BCA) method using bovine serum albumin (BSA) as a standard.

SDS-PAGE and Western Immunoblotting

Proteins were separated on 10% SDS-PAGE gels under reducing conditions and immunoblotted for detection of CYP450 isoenzymes using modifications of previously reported methods, Harris, et al., *P.N.A.S., U.S.A.* 88: 1407–1410, 1991. Proteins were loaded at 50 μg/lane and resolved under constant current (250 V) for approximately 4 hr at 2° C. Proteins were transferred to nitrocellulose membranes in 15 mM Tris buffer containing 120 mM glycine and 20% (v/v) methanol. The nitrocellulose membranes were blocked with 2.5% BSA and immunoblotted for CYP450 isoenzymes using primary monoclonal and polyclonal antibodies and secondary alkaline phosphatase conjugated anti-IgG. Immunoblots were developed with the Bio-Rad alkaline phosphatase substrate kit.

Microsomal Enzyme Activity Measures

All microsomal protein samples were compared to positive control microsomes with known enzymatic activities.

p-Nitrophenol Hydroxylation. The hydroxylation of p-nitrophenol was measured spectrophotometrically as described by Koop, *Chem. Res. Toxicol.* 3: 377–383, 1990. The generation of 4-nitrocatechol was determined from the absorbance at 546 nm as based on an extinction coefficient of 9.52 mM$^{-1}$ cm$^{-1}$. A DW2C dual-beam spectrophotometer was used for these determinations.

7-Ethoxyresorufin O-Dealkylation (EROD) and 7-Pentoxyresorufin O-Dealkylation (PROD). The O-dealkylation of 7-ethoxyresorufin and 7-pentoxyresorufin was measured fluorometrically using the methods described by Burke, et al., *Biochem. Pharmacol.* 34: 3337–3345, 1985, with minor modifications, Dutton, et al., *Arch. Biochem. Biophys.* 268: 617–629, 1989. The amount of resorufin generated was measured fluorometrically ($\lambda_{ex} \approx 535$ nm, $\lambda_{ex} \approx 585$ nm).

Testosterone Oxidation. The oxidation of testosterone was determined by reverse-phase HPLC as described by Wood, et al. *J. Biol. Chem.* 258: 8839–8847, 1983, Sonderfan, et al., *Arch. Biochem. Biophys.* 255: 27–41, 1987, and Sonderfan, et al., *Arch. Biochem. Biophys.* 265: 208–218, 1988. Testosterone, androstenedione, 6-dehydrotestosterone and 12-hydroxytestosterone isomers (i.e., 6α-, 15β-, 6β-, 15α-, 7α-, 16α-, 16β-, 1β-, 18-, 11β-, 2α- and 2β-hydroxytestosterone) were resolved on a Supelcosil LC-18 octyldecylsilane (C$_{18}$) column and quantitated by integration of peak areas.

Lauric Acid Hydroxylation. The rate of lauric acid hydroxylation was determined by a combination of the radiometric partition method of Giera and van Lier, *Fund. Appl. Toxicol.* 16: 348–355, 1991, and the radiometric HPLC method of Romano, et al., *Anal. Biochem.* 170: 83–93, 1988. The rate of lauric acid hydroxylation was measured as the rate of conversion of [$^{14}$C]-lauric acid to 11- and 12-hydroxylauric acid. Abbreviations: NCE, new chemical entities; ECM, extracellular matrix; DMEM, Dulbecco's Modified Eagel Medium; DMSO, dimethyl sulfoxide; CYP450, cytochrome P450; RT-PCR, reverse transcriptase-polymerase chain reaction; mRNA, messenger ribonucleic acid; PB, phenobarbital; HC, hydrocortisone-21-hemisuccinate; 3MC, 3-methylcholanthrene; CLO, clofibrate; FACO, fatty acyl-CoA oxidase; CYC, cyclophilin; UDPGT-PB, uridine diphosphate-glucuronosyltransferase (phenobarbital inducible form); GST-Ya, glutathione-S-transferase-Ya; ST, rat sulfotransferase.

Results

The oligonucleotide PCR primers used to amplify rat CYP450 1A1, 1A2, 2B1/2, 2C11, 2E1, 3A1, 3A2, 4A1, fatty acyl-CoA oxidase (FACO) and cyclophilin cDNA are as described above. The house-keeping gene, cyclophilin (Cavicchioli, et al., *Mol. Brain Res.* 9: 319–325, 1991), was used to determine the constitutive level of gene transcription and to control for variations in RNA recoveries from each liver specimen. Normalization was accomplished by quantitating the amount of amplified cDNA products by scanning laser densitometry and calculating the ratio of the amount of each enzyme cDNA relative to the amount of cyclophilin (CYC) cDNA (i.e., the enzyme cDNA O.D.:CYC cDNA O.D.). This enzyme:cyclophilin ratio was generated for each CYP450 isoenzyme and used to compare the relative amounts of CYP450 isoenzyme mRNA in each liver.

Analysis of CYP1A1 and CYP1A2 Expression

The expression of CYP1A1 and CYP1A2 mRNA following exposure to various inducers of CYP450 is presented in FIGS. 1 and 3a–3d. Under linear amplification conditions, expression of the CYP1A1 and CYP1A2 mRNA was not detected in the livers of water (H$_2$O) and corn oil (CO) treated control rats. The expression of both genes was found to be noticeably increased following exposure of rats to the prototypical CYP1A inducer, β-naphthoflavone (BNF). One of 3 rats appeared to have a slight increase in CYP1A2 expression in response to dexamethasone (DEX) in this experiment. No other treatments were found to change the expression of CYP1A1 or CYP1A2 at the mRNA level.

FIGS. 2 and 3c illustrate the detection of the CYP1A1 protein by Western immunoblotting of microsomal protein fractions isolated from these livers. These results demonstrate close agreement in the detection of CYP1A1 gene expression by the two techniques. A slight increase in CYP1A1 protein was observed in the livers of the phenobarbital (PB) treated rats (FIG. 3c). This increase in CYP1A1 expression was confirmed by an increase in microsomal EROD activity (FIG. 3d). CYP1A1 protein was found to be markedly increased after 3MC treatment.

Results of the analysis of microsomal EROD activity in the livers of exposed rats confirmed the induction of CYP1A1 by BNF at both the mRNA and protein levels and the induction of CYP1A1 by PB at the protein level (FIG. 3d). No other chemical treatments were found to cause an increase in liver EROD activity over control levels.

Analysis of CYP2B1/2 Expression

The combined expression of CYP2B1 and CYP2B2 mRNA in male rat liver following exposure to the various CYP450 inducers is presented in FIGS. 1 and 3e–3h. These two enzymes have a 97% sequence homology and are co-regulated by chemical inducers of this CYP450 subfamily. The oligonucleotide primers used in this study do not distinguish between the two CYP2B isoenzymes.

CYP2B1/2 mRNA was found to be constitutively present in control (H$_2$O and CO treated) rat livers (FIGS. 1 and 3e). Following exposure of rats to PB, a prototypical CYP2B inducer, expression of CYP2B1/2 mRNA was found to increase noticeably relative to control. Metyrapone (MET), hydrocortisone-21-hemisuccinate (HC) and clofibrate (CLO) were also found to cause an increase the expression of CYP2B1/2 mRNA relative to their respective controls.

Similar results were obtained using Western immunoblotting for expression of the CYP2B1 apoprotein in rat liver microsomal protein fraction (FIG. 3f). The CYP2B1 apoprotein was found to be constitutively expressed at a relatively low level in control rat livers and inducibly increased following exposure to PB. Likewise, MET and CLO (to a lesser extent) were also found to cause an increase in the expression of the CYP2B1 apoprotein.

These findings were further confirmed by analysis of microsomal PROD and testosterone 16-beta-hydroxylase activity in the livers of chemically exposed rats (FIGS. 3g and 3h). Increases in PROD and testosterone 16-beta-hydroxylase activity were detected in both the PB and MET treated livers. CLO was not found to increase microsomal PROD activity in these livers. Induction of CYP2B at the mRNA and protein levels was determined to be extremely weak and likely to be below the level of detection by enzymatic assay techniques.

Analysis of CYP2C11

High levels of mRNA expression of the adult male specific CYP450 isoenzyme, CYP2C11, were detected in control ($H_2O$ and CO) rat livers (FIGS. 1 and 3i). Following exposure of rats to BNF (and MET to a lesser extent), a decreased expression of CYP2C11 mRNA was observed. None of the chemical treatments used in these studies were found to increase CYP2C11 mRNA, confirming the high level constitutive expression of this enzyme in the male rat.

Western immunoblot analysis of microsomal protein fractions for CYP2C11 apoprotein expression also demonstrated the high level constitutive expression of this enzyme in control rats and a decreased expression following exposure of animals to BNF (FIGS. 3j and 3i). DEX was also found to have a slight effect on CYP2C11 protein. This effect of DEX was not observed at the mRNA level.

Analysis of microsomal testosterone 2-alpha-hydroxylase (T2aH) activity also showed considerable CYP2C11 enzyme activity present in control rat livers which was decreased following exposure to BNF (FIG. 3k). A slight decrease was also observed in some of the rats exposed to DEX, confirming the decrease observed in apoprotein in these livers. In contrast to both the mRNA and protein determinations, T2aH activity was also found to be decreased in the livers of animals exposed to PB.

Analysis of CYP2E1 Expression

Analysis of CYP2E1 mRNA demonstrated a high level constitutive expression in control male rat livers (FIG. 1 and 3l). Following exposure to the various prototypical CYP450 inducers, both HC and CLO were found to increase CYP2E1 expression at the mRNA level. Moderate increases in CYP2E1 apoprotein were also observed with HC and CLO and 3MC. In some experiments CLO was found to cause a 2–3 fold increase in CYP2E1 mRNA expression. No other chemical treatments were found to affect the expression of CYP2E over control levels.

As with mRNA, high levels of CYP2E1 apoprotein were found to be expressed in control rat liver (FIGS. 2 and 3m). However, none of the compound treatments, including CLO, were found to cause a consistent effect on the levels of CYP2E1 apoprotein. BNF was found to cause a slight, but consistent, reduction in the levels of CYP2E1 apoprotein.

Two microsomal enzyme activities were monitored to assess the induction of CYP2E1 activity, p-Nitrophenol hydroxylase (pNPH) and lauric acid 11-hydroxylase (LA-11-H) (FIGS. 3n and 3o). Although they are each indicative of CYP2E1 activity, neither is specific for the CYP2E1 enzyme. The activity of pNPH was found to closely parallel the induction of CYP2E1 protein, where PB and MET treatments both caused increases in enzyme activity. In addition, BNF was found to cause a marked reduction in pNPH activity. LA-11-H activity was also found to be increased by PB and decreased by BNF treatments but was not found to be increased by CLO exposure which reflects the ability of this compound to induce the CYP4A subfamily of enzymes. pNPH activity has been demonstrated to more accurately assess CYP2E1 enzyme expression than LA-11-H.

Analysis of CYP3A1 and CYP3A2 Expression

CYP3A1 was found to be constitutively expressed in control male rat liver (FIGS. 1 and 3p–3s) whereas CYP3A2 was found to be almost undetectable in this cell culture system. Following exposure of rat hepatocytes to HC, increase in both CYP3A1 and CYP3A2 mRNA levels was observed as compared to vehicle controls. PB was also found to cause an increase in the expression of the CYP3A1 (and to much lesser extent, CYP3A2) mRNA levels relative to vehicle controls. Both HC and PB were also found to increase CYP3A1 apoprotein expression as detected by western immunoblotting (FIGS. 2 and 3k). CLO was also found to cause slight elevations (two fold over control) in the expression of CYP3A1 at both the mRNA and protein levels. Analysis of CYP3A2 protein expression was not determined in this study. 3MC did not cause an increase in the expression of CYP3A1 or CYP3A2 at either the mRNA or protein level than CYP3A1. Following exposure to PB, MET, DEX and CLO, CYP3A1 mRNA was found to be increased relative to control whereas CYP3A2 mRNA expression was only increased in CLO exposed livers.

Western immunoblot analysis of liver microsomal protein fractions for CYP3A1 apoprotein showed a similar profile of expression for this enzyme (FIG. 3r). As indicated by the expression of CYP3A1 mRNA, PB, MET and DEX exposures all resulted in marked increases in the apparent levels of the CYP3A1 apoprotein.

Analysis of liver testosterone 6-beta-hydroxylase (T6bH) activity supports the changes in CYP3A mRNA and apoprotein expression (FIG. 3s). Although CLO was not found to cause an apparent increase in the levels of liver CYP3A1 protein in this experiment, the induction of CYP3A1 mRNA was confirmed by an increase in T6bH enzyme activity.

Analysis of CYP4A1 and FACO Expression

CYP4A1 and fatty acyl-CoA oxidase (FACO) mRNA were both found to be constitutively expressed in control male rat livers (FIGS. 1, 3t and 3w). Following exposure to CLO, a prototypical CYP4A1 inducer, both CYP4A1 and FACO mRNA were increased. DEX caused only a slight increase in CYP4A1 mRNA expression (FIG. 1 and 3t) and was not found to affect the expression of FACO.

A similar profile of CYP4A1 expression was found using Western immunoblot analysis of microsomal protein fractions were CLO was found to cause a marked increase in the expression of the CYP4A1 apoprotein (FIG. 3u). DEX was not found to cause any increase in the CYP4A1 apoprotein. Increased CYP4A1 expression by CLO was further demonstrated by an increase in lauric acid 12-hydroxylase (LA-12-H) activity in liver microsomal protein fractions from exposed rats (FIG. 3v).

EXAMPLE 2

(Application Using an In Vitro Test System)

Male Sprague-Dawley rats between the ages of 6–8 weeks and weighing 200–250 g were used in these studies. Food and water were available ad libitum.

Chemicals and Reagents

Cell culture materials. Cell culture medium was obtained from Gibco BRL (Grand Island, N.Y.). Collagenase type II was purchased from Worthington Biochemicals (Freehold, N.J.). Matrigel® was obtained from Collaborative Biomedical Products (Bedford, Mass.). Percoll was obtained from Pharmacia Biotech (Uppsala, Sweden). Hydrocortisone-21-hemisuccinate, insulin, heat inactivated newborn bovine serum, bovine albumin and the antibiotic-antimycotic solution were obtained from Sigma (St. Louis, Mo.). All other chemicals were of the highest grade available and purchased from Sigma. Tissue culture dishes (6 well plates) were obtained from Costar (Cambridge, Mass.). RNA STAT[60] (total RNA isolation reagent) was purchased from Leedo Medical Laboratory (Houston, Tex.).

RT-PCR and Western Immunoblotting. The oligonucleotide PCR primers for the amplification of rat CYC and CYP2B1 primers used here differ from those previously reported for the following reasons. The CYC primers previously used were designed to selectively amplify rat cyclophilin cDNA. The primers according to the present invention are non-species selective and have been used to produce an equal length amplification product of mouse, rat, dog, hamster, monkey and human cyclophilin. The CYP2B primers previously used were non-selective for the rat cytochrome CYP2B enzymes and were unable to distinguish the CYP2B1 and CYP2B2 enzyme cDNAs (e.g. CYP2B1/2 non-selective). The inventors' primers used to amplify CYP2B have been designed to selectively amplify the rat CYP2B1 enzyme.

Cell Culture Medium Preparation: The culture medium used in this study was specially formulated Dulbecco's Modified Eagel Medium (DMEM) with arginine free buffer, catalog #87-5128, as previously reported by Davila et al. The stock culture medium (DMEM) was supplemented at all times with hydrocortisone (0.1 $\mu$M), insulin (1 $\mu$M) and sodium bicarbonate (2 g/L). This serum free medium preparation was complemented with albumin and antibiotics and used to prepare the Matrigel® suspension as described below.

Hepatocyte Isolation and Culturing

The procedure for the isolation and primary culture of parenchymal hepatocytes from rat liver was based on the two step collagenase perfusion technique described by Seglen. Several modifications have been made to improve the culturing of the cell as indicated below.

The hepatocyte isolation procedure utilizes a retrograde perfusion of the liver via a catheter inserted through the right atrium and into the inferior vena cave. A peristaltic pump was used to perfuse the liver with two buffer solutions: 1) a calcium and magnesium-free salt solution (BSS, pH 7.4) containing sodium chloride (8.3 g/L), potassium chloride (0.5 g/L) and HEPES (2.4 g/L) and 2) a dissociating buffer (pH 7.4) containing BSS and collagenase type II (100 U/mL). These solutions were maintained at 37° C. and allowed to run as waste through a cut made in the hepatic portal vein. A perfusion rate of 25 mL/min was maintained for both perfusates for about 10 minutes each.

After the perfusion was terminated, the liver was rapidly excised from the body cavity and transferred to a sterile beaker containing 200 mL of warm BSS. The liver was raked gently with a pair of blunt forceps. The cell suspension was then filtered through a sterile nylon mesh (100 $\mu$m) and collected in several 50 ml conical test tubes. Hepatocytes were centrifuged twice at 30× g for three minutes and then the final pellet was resuspended with 30 mL of DMEM solution. Ten mL of diluted Percoll solution (40% v/v) was underlayed in each tube containing the cell suspension and then centrifuged at 1100× g for 15 minutes. The pellets were washed twice with DMEM at 30× g for 3 min and then resuspended in 30 mL DMEM solution.

Viable and nonviable cells were counted using the trypan blue dye exclusion test and a hemocytometer. Viability of the isolated hepatocytes used in these studies was typically greater than 95%. A solution of diluted Matrigel® (0.35 mg/mL DMEM) containing newborn bovine serum (8% v/v), albumin (0.1% w/v) and an antibiotics/antimycotic solution (1% v/v) was prepared. The final cell suspension was resuspended in this diluted Matrigel® solution to a final cell density of $4 \times 10^5$ cells/mL. A total of $8 \times 10^5$ cells were plated per well (2 mL total volume) in 6 well culture plates.

The entire perfusion protocol from anesthesia to cell plating was completed within 2 hr. Hepatocytes were incubated for three days in a humidified environment (95%) containing 5% $CO_2$. Hepatocytes were replenished with fresh serum free-medium containing Matrigel® (0.35 mg/mL), albumin (0.1% w/v) and the antibiotics/antimycotic solution (0.1% v/v) at 2 hr and 24 hr after plating. At 48 hr, the cultures were replenished with plain DMEM medium without Matrigel®, albumin or antibiotic/antimycotic for the remainder of the cell culture period.

Cell Culture Treatments

Hepatocytes were treated with PB (100 $\mu$M), HC (20 $\mu$M), 3MC (1 $\mu$M), and CLO (100 $\mu$M). PB and HC were dissolved in DMEM whereas 3MC and CLO were dissolved in DMSO and then diluted with DMEM prior to administration to the cultures (final DMSO concentration was 0.1% v/v). DMSO at 0.1% v/v, under the culture conditions described above, does not affect cell viability nor mRNA expression of the enzymes tested in this study (data not shown). The concentration of inducers used in these studies were selected based on preliminary experiments to determine the concentration of inducer producing maximal levels of enzyme expression (data not shown).

Isolation of Total RNA

At the end of the treatment period, 72 hr after culture initiation, cultured hepatocytes (2 dishes per treatment) were rinsed with ice cold phosphate buffer saline (PBS) and harvested for total RNA or protein. Total RNA was extracted and measured as previously described using RNA STAT[60] reagent [33].

Microsomes and Total Protein preparation

Microsomes and total protein were prepared as described by Morris et al. using a total of 5 cultured plates (6 well plates) per treatment.

Semi-Quantitative RT-PCR and Western Immunoblotting

RT-PCR and western immunoblotting analysis of total RNA and microsomal protein fractions for P450 enzyme expression were carried out as previously described. For the western immunoblotting of P450 enzymes, specific protein bands were detected using enhanced chemiluminescence reagent (DuPont NEN Research Product, Boston, Mass.). All studies were repeated a minimum of five times and representative data are presented.

Results

Normalization of the data was accomplished by quantitating the amount of amplified cDNA products by scanning laser densitometry (e.g. optical density, O.D.) and calculating the ratio of the amount of each enzyme cDNA relative to the amount of CYC cDNA. FIG. 1 illustrates the results obtained using RT-PCR to assess the levels of CYP450, FACO, UDPGT, ST, GST-Ya and CYC mRNA in rat hepatocytes exposed to various inducers of CYP450. The results are presented in a series of graphs (FIG. 3) that normalize the results obtained for each gene product to that of the housekeeping gene, CYC (i.e., enzyme O.D.:CYC O.D. ratio). Results obtained from western immunoblotting are compared to those curtained with RT-PCR for the detection of CYP450 expression (FIGS. 2 and 3).

The inventors confirmed that cell viability and composition of both the extracellular matrix and the culture medium are critical for the maintenance of multiple liver-specific functions in cultured rat hepatocytes both at the mRNA and protein levels. The inventors determined that the induction of hepatic CYP450, as well as Phase II conjugating enzymes, by drugs and chemicals are markedly enhanced by the following conditions: 1) high percent viability of isolated parenchymal cells (>94%), 2) adding insulin (1 µM) and hydrocortisone (100 nM) to the serum-free culture medium, which at these concentrations, are not effective inducing agents of the enzymes assessed in this study, 3) resuspending the hepatocytes directly into a diluted Matrigele solution and then plating them in a non-extracellular matrix-coated culture dish; the optimum concentration of Matrigel® in these studies being found to be 0.35 mg/mL, 4) replenishing the cells with fresh diluted Matrigel® in a serum-free medium at 2 hr and 24 hr after plating, and 5) adding the xenobiotics or CYP450 enzyme inducers at 24 and 48 hr after plating. Applicants found that a continuous 48 hr exposure to these enzyme inducing agents results in the induction of enzyme expression at both the mRNA and protein levels. Under these culture conditions, hepatocytes remain responsive to enzyme inducers for a minimum of one week.

In concentration-ranging studies using 3MC (1.1 µM to 10 µM), PB (1 µM to 2 mM), HC (1 µM to 100 µM) and CLO (1 µM to 2 mM), it was established that hepatocytes were responsive to chemical enzyme inducers in a dose-related fashion as early as 24 hr after initial plating. Results from these studies were as follows: 1) 3MC increased expression of CYP1A1 and CYP1A2 mRNAs at concentrations as low as 0.1 µM with an optimum concentration at 1 µM, 2) PB caused a marked induction of the CYP2B1 enzyme mRNA at concentrations as low as 10 µM, with maximum induction occurring at a concentration of 100 µM, 3) HC induced CYP3A1 and CYP3A2 (to a much lesser degree) mRNAs expression at concentrations as low as 10 µM, with a maximum induction occurring at a concentration of 20 µM, and 4) CLO increased CYP4A1 at concentrations as low as 20 µM, with maximum induction occurring at a concentration of 100 µM. The optimum concentrations for these inducing agents were used for mRNA and protein expression analysis in this study. Cell viability (>95%) was measured at the beginning and at the end of the experiments using the trypan blue dye exclusion test and cytosolic enzyme leakage assays, including lactate dehydrogenase (LDH), alanine aminotransferases (ALT) and sorbitol dehydrogenase (SDH).

Analysis of UDPGT, GST-Ya, and ST Expression

UDPGT, GST-Ya and ST mRNA was found to be constitutively expressed in rat hepatocytes cultured on Matrigel®, as indicated in FIGS. 1 and 3x–z. UDPGT was found to be markedly increased following exposure to PB and HC as compared to vehicle control cells. GST-Ya mRNA expression was found to be increased following exposure to 3MC, PB, and CLO and ST mRNA was induced by HC. Analysis of UDPGT, GST-Ya and ST protein expression was not determined.

Although the present invention has been illustrated with reference to certain preferred embodiments, it will be appreciated that the present invention is not limited to the specifics set forth therein. Those skilled in the art readily will appreciate numerous variations and modifications within the spirit and scope of the present invention, and all such variations and modifications are intended to be covered by the present invention, which is defined by the following claims.

What is claimed is:

1. A primer set for specifically detecting expression of DNA encoding cytochrome P450 isoenzyme 1A1 in a tissue following exposure to drugs or chemicals, the primer set comprising: oligonucleotides which consist essentially of CTGGTTCTGGATACCCAGCTG (SEQ ID NO:1) and CCTAGGGTTGGTTACCAGG (SEQ ID NO:2).

2. A primer set for specifically detecting expression of DNA encoding cytochrome P450 isoenzyme 1A2 in a tissue following exposure to drugs or chemicals, the primer set comprising: oligonucleotides which consist essentially of GTCACCTCAGGGAATGCTGTG (SEQ ID NO:3) and GTTGACAATCTTCTCCTGAGG (SEQ ID NO:4).

3. A primer set for specifically detecting expression of DNA encoding cytochrome P450 isoenzyme 2B1/2 in a tissue following exposure to drugs or chemicals, the primer set comprising: oligonucleotides which consist essentially of GAGTTCTTCTCTGGGTTCCTG (SEQ ID NO:5) and ACTGTGGGTCATGGAGAGCTG (SEQ ID NO:6).

4. A primer set for specifically detecting expression of DNA of cytochrome P450 isoenzyme 2C11 in a tissue following exposure to drugs or chemicals, the primer set comprising: oligonucleotides which consist essentially of CTGCTGCTGCTGAAACACGTG (SEQ ID NO: 7) and GGATGACAGCGATACTATCAC (SEQ ID NO:8).

5. A primer set for specifically detecting expression of DNA encoding cytochrome P450 isoenzyme 2E1 in a tissue following exposure to drugs or chemicals, the primer set comprising: oligonucleotides which consist essentially of CTCCTCGTCATATCCATCTG (SEQ ID NO:9) and GCAGCCAATCAGAAATGTGG (SEQ ID NO:10).

6. A primer set for specifically detecting expression of DNA encoding cytochrome P450 isoenzyme 3A1 in a tissue following exposure to drugs or chemicals, the primer set comprising: oligonucleotides which consist essentially of ATCCGATATGGAGATCAC (SEQ ID NO:11) and GAA-GAAGTCCTTGTCTGC (SEQ ID NO:12).

7. A primer set for specifically detecting expression of DNA encoding cytochrome P450 isoenzyme 3A2 in a tissue following exposure to drugs or chemicals, the primer set comprising: oligonucleotides which consist essentially of CGACTTGGAACCCATAGAC (SEQ ID NO:13) and GGCTTAGGGAGATTTGACATG (SEQ ID NO:14).

8. A primer set for specifically detecting expression of DNA of cytochrome P450 isoenzyme 4A1 in a tissue following exposure to drugs or chemicals, the primer set comprising: oligonucleotides which consist essentially of GGTGACAAAGAACTACAGC (SEQ ID NO:15) and AGAGGAGTCTTGACCTGCCAG (SEQ ID NO:16).

9. A primer set for specifically detecting expression of DNA of cytochrome P450 isoenzyme 2B1 in a tissue following exposure to drugs or chemicals, the primer set comprising: oligonucleotides which consist essentially of CAACCCTTGATGACCGCAGT (SEQ ID NO:23) and GGAAGTGTTCAGGATTGAAGC (SEQ ID NO:24).

10. A method for specifically detecting expression of DNA encoding a target enzyme selected from the group consisting of cytochrome P450 isoenzymes 1A1, 1A2, 2B1, 2B1/2, 2C11, 2E1, 3A1, 3A2, or 4A1 in a tissue following exposure to drugs or chemicals, the method comprising the steps of:

a) providing a sample of RNA extracted from the tissue;
b) converting the sample of RNA to cDNA using reverse transcriptase and oligo d(T)$_{15-18}$, primers;
c) amplifying the cDNA using polymerase chain reaction and a primer set of any one of claims 1–8 and 9 to provide amplified cDNA; and
d) separating and detecting the amplified cDNA to detect expression of said target enzyme.

11. The method of claim 10, wherein said RNA is extracted from rat liver.

* * * * *

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
      (A) ORGANISM: Rattus norvegicus
      (F) TISSUE TYPE: Liver
      (G) CELL TYPE: Hepatocyte (viii) POSITION IN GENOME:
      (C) UNITS: bp (xi) SEQUENCE DESCRIPTION: SEQ ID NO:1:

CTGGTTCTGG ATACCCAGCT G          21

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:2:

CCTAGGGTTG GTTACCAGG                                                    19

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:3:

GTCACCTCAG GGAATGCTGT G                                                 21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:

(C) UNITS: bp (xi) SEQUENCE DESCRIPTION: SEQ ID NO:4:

GTTGACAATC TTCTCCTGAG G                                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:5:

GAGTTCTTCT CTGGGTTCCT G                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:6:

ACTGTGGGTC ATGGAGAGCT G                                              21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO

```
          (v) FRAGMENT TYPE: internal (vi) ORIGINAL SOURCE:
              (A) ORGANISM: Rattus norvegicus
              (F) TISSUE TYPE: Liver
              (G) CELL TYPE: Hepatocyte (viii) POSITION IN GENOME:
              (C) UNITS: bp (xi) SEQUENCE DESCRIPTION: SEQ ID NO:7:

CTGCTGCTGC TGAAACACGT G                                              21

(2) INFORMATION FOR SEQ ID NO:8:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
              (A) ORGANISM: Rattus norvegicus
              (F) TISSUE TYPE: Liver
              (G) CELL TYPE: Hepatocyte (viii) POSITION IN GENOME:
              (C) UNITS: bp (xi) SEQUENCE DESCRIPTION: SEQ ID NO:8:

GGATGACAGC GATACTATCA C                                              21

(2) INFORMATION FOR SEQ ID NO:9:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
              (A) ORGANISM: Rattus norvegicus
              (F) TISSUE TYPE: Liver
              (G) CELL TYPE: Hepatocyte (viii) POSITION IN GENOME:
              (C) UNITS: bp (xi) SEQUENCE DESCRIPTION: SEQ ID NO:9:

CTCCTCGTCA TATCCATCTG                                                20

(2) INFORMATION FOR SEQ ID NO:10:

(i) SEQUENCE CHARACTERISTICS:
              (A) LENGTH: 20 base pairs
              (B) TYPE: nucleic acid
              (C) STRANDEDNESS: single
```

```
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:10:

GCAGCCAATC AGAAATGTGG                                                  20

(2) INFORMATION FOR SEQ ID NO:11:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:11:

ATCCGATATG GAGATCAC                                                    18

(2) INFORMATION FOR SEQ ID NO:12:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:12:

GAAGAAGTCC TTGTCTGC                                                    18
```

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:13:

CGACTTGGAA CCCATAGAC                                         19

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:14:

GGCTTAGGGA GATTTGACAT G                                   21

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver (G) CELL TYPE: Hepatocyte (viii) POSITION IN GENOME:
            (C) UNITS: bp (xi) SEQUENCE DESCRIPTION: SEQ ID NO:15:

GGTGACAAAG AACTACAGC                                                     19

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
            (A) ORGANISM: Rattus norvegicus
            (F) TISSUE TYPE: Liver
            (G) CELL TYPE: Hepatocyte (viii) POSITION IN GENOME:
            (C) UNITS: bp (xi) SEQUENCE DESCRIPTION: SEQ ID NO:16:

AGAGGAGTCT TGACCTGCCA G                                                  21

(2) INFORMATION FOR SEQ ID NO:17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
            (A) ORGANISM: Rattus norvegicus
            (F) TISSUE TYPE: Liver
            (G) CELL TYPE: Hepatocyte (viii) POSITION IN GENOME:
            (C) UNITS: bp (xi) SEQUENCE DESCRIPTION: SEQ ID NO:17:

CTGTTATGAT GCTGCAGACA GC                                                 22

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
             (A) ORGANISM: Rattus norvegicus
             (F) TISSUE TYPE: Liver
             (G) CELL TYPE: Hepatocyte (viii) POSITION IN GENOME:
             (C) UNITS: bp (xi) SEQUENCE DESCRIPTION: SEQ ID NO:18:

ACACAGGTTC CTCAGCACAG                                                       20

(2) INFORMATION FOR SEQ ID NO:19:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
             (A) ORGANISM: Rattus norvegicus
             (F) TISSUE TYPE: Liver
             (G) CELL TYPE: Hepatocyte (viii) POSITION IN GENOME:
             (C) UNITS: bp (xi) SEQUENCE DESCRIPTION: SEQ ID NO:19:

CTTCGACATC ACGGCTGATG G                                                     21

(2) INFORMATION FOR SEQ ID NO:20:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
             (A) ORGANISM: Rattus norvegicus
             (F) TISSUE TYPE: Liver
             (G) CELL TYPE: Hepatocyte (viii) POSITION IN GENOME:
             (C) UNITS: bp (xi) SEQUENCE DESCRIPTION: SEQ ID NO:20:

CAGGACCTGT ATGCTTCAGG                                                       20

(2) INFORMATION FOR SEQ ID NO:21:

(i) SEQUENCE CHARACTERISTICS:

```
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:21:

CTTGTCCATG GCAAATGCTG                                           20

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp (xi) SEQUENCE DESCRIPTION: SEQ ID NO:22:

GTGATCTTCT TGCTGGTCTT GC                                        22

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
        (A) ORGANISM: Rattus norvegicus
        (F) TISSUE TYPE: Liver
        (G) CELL TYPE: Hepatocyte (viii) POSITION IN GENOME:
        (C) UNITS: bp
```

```
        (xi) SEQUENCE DESCRIPTION: SEQ ID NO:23:

CAACCCTTGA TGACCGCAGT                                                         20

(2) INFORMATION FOR SEQ ID NO:24:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
            (A) ORGANISM: Rattus norvegicus
            (F) TISSUE TYPE: Liver
            (G) CELL TYPE: Hepatocyte (viii) POSITION IN GENOME:
            (C) UNITS: bp (xi) SEQUENCE DESCRIPTION: SEQ ID NO:24:

GGAAGTGTTC AGGATTGAAG C                                                       21

(2) INFORMATION FOR SEQ ID NO:25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
            (A) ORGANISM: Rattus norvegicus
            (F) TISSUE TYPE: Liver
            (G) CELL TYPE: Hepatocyte (viii) POSITION IN GENOME:
            (C) UNITS: bp (xi) SEQUENCE DESCRIPTION: SEQ ID NO:25:

GCCTTCTCAC TGCCTTGAAG                                                         20

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA to mRNA (iii) HYPOTHETICAL: NO (iv) ANTI-SENSE: YES (v) FRAGMENT TYPE: internal
```

```
    (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:26:

GTCTTACGGC AACAAAAGAG GCAG                                                24

(2) INFORMATION FOR SEQ ID NO:27:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:27:

CTTGGCAAAA GACAGGACC                                                      19

(2) INFORMATION FOR SEQ ID NO:28:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:28:

GTTTTGCATC CATGGGAAGC                                                     20

(2) INFORMATION FOR SEQ ID NO:29:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

-continued

```
    (ii) MOLECULE TYPE: cDNA to mRNA (iii) HYPOTHETICAL: NO (iv) ANTI-SENSE: NO (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:29:

CTTCAGTTCC AAGGCCAAGG                                             20

(2) INFORMATION FOR SEQ ID NO:30:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA to mRNA (iii) HYPOTHETICAL: NO (iv) ANTI-SENSE: YES (v) FRAGMENT TYPE: internal (vi) ORIGINAL SOURCE:
         (A) ORGANISM: Rattus norvegicus
         (F) TISSUE TYPE: Liver
         (G) CELL TYPE: Hepatocyte (viii) POSITION IN GENOME:
         (C) UNITS: bp (xi) SEQUENCE DESCRIPTION: SEQ ID NO:30:

GTGAAGTGAT TCTTCCAGTC                                             20
```